US010610688B2

(12) United States Patent
Thakur et al.

(10) Patent No.: US 10,610,688 B2
(45) Date of Patent: Apr. 7, 2020

(54) SYSTEMS AND METHODS FOR CLOSED-LOOP PAIN MANAGEMENT

(71) Applicant: Boston Scientific Neuromodulation Corporation, Valencia, CA (US)

(72) Inventors: Pramodsingh Hirasingh Thakur, Woodbury, MN (US); Jianwen Gu, Valencia, CA (US); Bryan Allen Clark, Forest Lake, MN (US); David J. Ternes, Roseville, MN (US); David L. Perschbacher, Coon Rapids, MN (US); James John Kleinedler, Plymouth, MN (US); Elizabeth M. Annoni, White Bear Lake, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 178 days.

(21) Appl. No.: 15/711,578

(22) Filed: Sep. 21, 2017

(65) Prior Publication Data

US 2018/0085584 A1    Mar. 29, 2018

Related U.S. Application Data

(60) Provisional application No. 62/400,313, filed on Sep. 27, 2016.

(51) Int. Cl.
*A61N 1/36* (2006.01)
*A61B 5/00* (2006.01)
(Continued)

(52) U.S. Cl.
CPC ........ *A61N 1/36071* (2013.01); *A61B 5/4824* (2013.01); *A61B 5/4836* (2013.01);
(Continued)

(58) Field of Classification Search
CPC .................. A61N 1/36071; A61N 1/36062
(Continued)

(56) References Cited

U.S. PATENT DOCUMENTS

| 4,297,685 A | 10/1981 | Brainard, II |
| 5,187,675 A | 2/1993 | Dent et al. |

(Continued)

FOREIGN PATENT DOCUMENTS

| EP | 1897586 A1 | 3/2008 |
| RU | 2559783 C1 | 8/2015 |

(Continued)

OTHER PUBLICATIONS

U.S. Appl. No. 15/687,925, filed Aug. 28, 2017, Method and Apparatus for Pain Management Using Heart Sounds.
(Continued)

*Primary Examiner* — Nadia A Mahmood
(74) *Attorney, Agent, or Firm* — Schwegman Lundberg & Woessner, P.A.

(57) ABSTRACT

Systems and methods for managing pain in patient are described. A system may include sensors configured to sense physiological or functional signals, and a pain analyzer to generate signal metrics from the physiological or functional signals. The pain analyzer also generates weight factors corresponding to the signal metrics. The weight factors may indicate the signal metrics reliability in representing an intensity of the pain. The pain analyzer generates a pain score using a plurality of signal metrics and a plurality of weight factors. The pain score may be output to a user or a process. The system may additionally include an electrostimulator to generate and deliver closed-loop pain therapy according to the pain score.

20 Claims, 8 Drawing Sheets

(51) Int. Cl.
*A61B 7/04* (2006.01)
*A61N 1/05* (2006.01)

(52) U.S. Cl.
CPC ............ *A61B 7/04* (2013.01); *A61N 1/36062* (2017.08); *A61N 1/36135* (2013.01); *A61N 1/36139* (2013.01); *A61N 1/0551* (2013.01)

(58) Field of Classification Search
USPC .......................................................... 607/46
See application file for complete search history.

(56) References Cited

U.S. PATENT DOCUMENTS

| | | | |
|---|---|---|---|
| 5,774,591 A | 6/1998 | Black et al. | |
| 6,016,103 A | 1/2000 | Leavitt | |
| 6,076,011 A | 6/2000 | Hoover | |
| 6,088,040 A | 7/2000 | Oda et al. | |
| 6,173,260 B1 | 1/2001 | Slaney | |
| 6,480,734 B1 | 11/2002 | Zhang et al. | |
| 6,497,658 B2 | 12/2002 | Roizen et al. | |
| 6,654,632 B2 | 11/2003 | Lange et al. | |
| 6,659,968 B1 | 12/2003 | McClure | |
| 6,731,984 B2 | 5/2004 | Cho et al. | |
| 6,871,099 B1 | 3/2005 | Whitehurst et al. | |
| 7,001,337 B2 | 2/2006 | Dekker | |
| 7,004,907 B2 | 2/2006 | Banet et al. | |
| 7,177,686 B1 | 2/2007 | Turcott | |
| 7,189,204 B2 | 3/2007 | Ni et al. | |
| 7,222,075 B2 | 5/2007 | Petrushin | |
| 7,299,086 B2 | 11/2007 | McCabe et al. | |
| 7,376,457 B2 | 5/2008 | Ross | |
| 7,407,485 B2 | 8/2008 | Huiku | |
| 7,463,927 B1 | 12/2008 | Chaouat | |
| 7,566,308 B2 | 7/2009 | Stahmann | |
| 7,627,475 B2 | 12/2009 | Petrushin | |
| 7,636,602 B2 | 12/2009 | Baru Fassio et al. | |
| 7,650,184 B2 | 1/2010 | Walter | |
| 7,678,061 B2 | 3/2010 | Lee et al. | |
| 7,775,993 B2 | 8/2010 | Heruth et al. | |
| 7,957,809 B2 | 6/2011 | Bourget et al. | |
| 7,986,991 B2 | 7/2011 | Prichep | |
| 8,019,439 B2 | 9/2011 | Kuzma et al. | |
| 8,055,348 B2 | 11/2011 | Heruth et al. | |
| 8,083,682 B2 | 12/2011 | Dalal et al. | |
| 8,192,376 B2 | 6/2012 | Lovett et al. | |
| 8,209,182 B2 | 6/2012 | Narayanan | |
| 8,290,596 B2 | 10/2012 | Wei et al. | |
| 8,332,038 B2 | 12/2012 | Heruth et al. | |
| 8,398,556 B2 | 3/2013 | Sethi et al. | |
| 8,447,401 B2 | 5/2013 | Miesel et al. | |
| 8,475,370 B2 | 7/2013 | McCombie et al. | |
| 8,529,459 B2 | 9/2013 | Malker et al. | |
| 8,606,356 B2 | 12/2013 | Lee et al. | |
| 8,688,221 B2 | 4/2014 | Miesel | |
| 8,744,587 B2 | 6/2014 | Miesel et al. | |
| 8,805,518 B2 | 8/2014 | King et al. | |
| 9,066,659 B2 | 6/2015 | Thakur et al. | |
| 9,072,870 B2 | 7/2015 | Wu et al. | |
| 9,119,965 B2 | 9/2015 | Xi et al. | |
| 9,314,168 B2 | 4/2016 | Watson et al. | |
| 9,395,792 B1 | 7/2016 | Kahn et al. | |
| 2004/0015091 A1 | 1/2004 | Greenwald et al. | |
| 2007/0167859 A1 | 7/2007 | Finneran et al. | |
| 2007/0213783 A1 | 9/2007 | Pless | |
| 2007/0260285 A1 | 11/2007 | Libbus et al. | |
| 2008/0177191 A1 | 7/2008 | Patangay et al. | |
| 2008/0249430 A1 | 10/2008 | John et al. | |
| 2009/0192556 A1 | 7/2009 | Wu et al. | |
| 2009/0312663 A1 | 12/2009 | John et al. | |
| 2009/0318986 A1 | 12/2009 | Alo et al. | |
| 2010/0016913 A1 | 1/2010 | Arcot-Krishnamurthy et al. | |
| 2010/0286549 A1 | 11/2010 | John et al. | |
| 2011/0015702 A1 | 1/2011 | Ternes et al. | |
| 2011/0021928 A1 | 1/2011 | Giovangrandi et al. | |
| 2011/0124979 A1 | 5/2011 | Heneghan et al. | |
| 2011/0137134 A1 | 6/2011 | Hemmerling et al. | |
| 2011/0172562 A1 | 7/2011 | Sahasrabudhe et al. | |
| 2011/0224749 A1 | 9/2011 | Ben-David et al. | |
| 2011/0306846 A1 | 12/2011 | Osorio | |
| 2013/0165994 A1 | 6/2013 | Ternes et al. | |
| 2013/0268016 A1 | 10/2013 | Xi et al. | |
| 2014/0276188 A1 | 9/2014 | Jardin | |
| 2014/0276549 A1 | 9/2014 | Osorio | |
| 2015/0005842 A1 | 1/2015 | Lee et al. | |
| 2015/0289803 A1 | 10/2015 | Wu et al. | |
| 2016/0022203 A1 | 1/2016 | Arnold et al. | |
| 2016/0082265 A1 | 3/2016 | Moffitt et al. | |
| 2016/0129272 A1 | 5/2016 | Hou et al. | |
| 2016/0144194 A1 | 5/2016 | Roothans et al. | |
| 2016/0243359 A1 | 8/2016 | Sharma | |
| 2016/0302720 A1 | 10/2016 | John et al. | |
| 2016/0374567 A1 | 12/2016 | Breslow et al. | |
| 2018/0078768 A1 | 3/2018 | Thakur et al. | |
| 2018/0085055 A1 | 3/2018 | Annoni et al. | |
| 2018/0110464 A1 | 4/2018 | Annoni et al. | |
| 2018/0192941 A1 | 7/2018 | Annoni et al. | |
| 2018/0192942 A1 | 7/2018 | Clark et al. | |
| 2018/0193644 A1 | 7/2018 | Annoni et al. | |
| 2018/0193650 A1 | 7/2018 | Srivastava et al. | |
| 2018/0193651 A1 | 7/2018 | Annoni et al. | |
| 2018/0193652 A1 | 7/2018 | Srivastava et al. | |
| 2018/0229040 A1 | 8/2018 | Srivastava et al. | |

FOREIGN PATENT DOCUMENTS

| | | |
|---|---|---|
| WO | WO-2007007058 A1 | 1/2007 |
| WO | WO-2009055127 A1 | 4/2009 |
| WO | WO-2010051406 A1 | 5/2010 |
| WO | WO-2011008747 A2 | 1/2011 |
| WO | WO-2011053607 A1 | 5/2011 |
| WO | WO-2013134479 A1 | 9/2013 |
| WO | WO-2014151860 A1 | 9/2014 |
| WO | WO-2015060888 A1 | 4/2015 |
| WO | WO-2015128567 | 9/2015 |
| WO | WO-2016077786 A1 | 5/2016 |
| WO | WO-2018052695 A1 | 3/2018 |
| WO | WO-2018063637 A1 | 4/2018 |
| WO | WO-2018063912 A1 | 4/2018 |
| WO | WO-2018080887 A1 | 5/2018 |

OTHER PUBLICATIONS

U.S. Appl. No. 15/688,676, filed Aug. 28, 2017, Method and Apparatus for Pain Management Using Objective Pain Measure.

"U.S. Appl. No. 15/687,925, Final Office Action dated Feb. 14, 2019", 10 pgs.

"U.S. Appl. No. 15/687,925, Non Final Office Action dated Jun. 11, 2019", 11 pgs.

"U.S. Appl. No. 15/687,925, Non Final Office Action dated Oct. 9, 2018", 9 pgs.

"U.S. Appl. No. 15/687,925, Response filed Jan. 9, 2019 to Non Final Office Action dated Oct. 9, 2018", 9 pgs.

"U.S. Appl. No. 15/687,925, Response filed May 13, 2019 to Final Office Action dated Feb. 14, 2019", 11 pgs.

"U.S. Appl. No. 15/688,676, Final Office Action dated Jul. 29, 2019", 7 pgs.

"U.S. Appl. No. 15/688,676, Non Final Office Action dated Jan. 11, 2019", 7 pgs.

"U.S. Appl. No. 15/688,676, Response filed Apr. 9, 2019 to Non Final Office Action dated Jan. 11, 2019", 12 pgs.

"U.S. Appl. No. 15/788,403, Non Final Office Action dated Jul. 23, 2019", 9 pgs.

"U.S. Appl. No. 15/867,756, Non Final Office Action dated Jul. 1, 2019", 8 pgs.

"U.S. Appl. No. 15/867,760, Non Final Office Action dated Jul. 1, 2019", 8 pgs.

"Australian Application Serial No. 2017325823, First Examination Report dated Jun. 19, 2019", 3 pgs.

"Australian Application Serial No. 2017334841, First Examination Report dated Jun. 24, 2019", 3 pgs.

(56) References Cited

OTHER PUBLICATIONS

"Australian Application Serial No. 2017335497, First Examination Report dated Jun. 26, 2019", 3 pgs.
"International Application Serial No. PCT/US2017/048867, International Preliminary Report on Patentability dated Mar. 28, 2019", 8 pgs.
"International Application Serial No. PCT/US2017/048867, International Search Report dated Nov. 13, 2017", 5 pgs.
"International Application Serial No. PCT/US2017/048867, Written Opinion dated Nov. 13, 2017", 6 pgs.
"International Application Serial No. PCT/US2017/048896, International Preliminary Report on Patentability dated Apr. 11, 2019", 8 pgs.
"International Application Serial No. PCT/US2017/048896, International Search Report dated Nov. 27, 2017", 5 pgs.
"International Application Serial No. PCT/US2017/048896, Written Opinion dated Nov. 27, 2017", 6 pgs.
"International Application Serial No. PCT/US2017/052685, International Preliminary Report on Patentability dated Apr. 11, 2019", 6 pgs.
"International Application Serial No. PCT/US2017/052685, International Search Report dated Jan. 4, 2018", 5 pgs.
"International Application Serial No. PCT/US2017/052685, Written Opinion dated Jan. 4, 2018", 6 pgs.
"International Application Serial No. PCT/US2017/057367, International Preliminary Report on Patentability dated May 9, 2019", 6 pgs.
"International Application Serial No. PCT/US2017/057367, International Search Report dated Jan. 19, 2018", 4 pgs.
"International Application Serial No. PCT/US2017/057367, Written Opinion dated Jan. 19, 2018", 4 pgs.
"International Application Serial No. PCT/US2018/013257, International Preliminary Report on Patentability dated Jul. 25, 2019", 8 pgs.
"International Application Serial No. PCT/US2018/013257, International Search Report dated Apr. 19, 2018", 4 pgs.
"International Application Serial No. PCT/US2018/013257, Written Opinion dated Apr. 19, 2018", 6 pgs.
Ambady, Nalini, et al., "Thin Slices of Expressive Behavior as Predictors of Interpersonal Consequences: A Meta-Analysis", Psychological Bulletin, 1992, vol. 111, No. 2, 256-274.
Annoni, Elizabeth M., et al., "Pain Management Based on Brain Activity Monitoring", U.S. Appl. No. 62/445,061, filed Jan. 11, 2017.
Annoni, Elizabeth M., et al., "Pain Management Based on Muscle Tension Measurements", U.S. Appl. No. 62/445,092, filed Jan. 11, 2017.
Annoni, Elizabeth M., et al., "Pain Management Based on Respiration-Mediated Heart Rates", U.S. Appl. No. 62/445,069, filed Jan. 11, 2017.
Annoni, Elizabeth M., et al., "Patient-Specific Calibration of Pain Quantification", U.S. Appl. No. 62/445,095, filed Jan. 11, 2017.
Bansevicius, Dalius, et al., "Mental stress of long duration: EMG activity, perceived tension, fatigue, and pain development in pain-free subjects", Headache: The Journal of Head and Face Pain; 37.8, (1997), 499-510.
Bartlett, Marian Stewart, et al., "Automatic Decoding of Facial Movements Reveals Deceptive Pain Expressions", Current Biology 24, 738-743, Mar. 31, 2014.
Berthomier, Christian, et al., "Automatic analysis of single-channel sleep EEG: validation in healthy individuals", Sleep—New York Then Westchester—30.11, (2007), 1587-1595.
Bunde, Armin, et al., "Correlated and uncorrelated regions in heart-rate fluctuations during sleep", Physical Review Letters 85.17, (2000), 3736-3739.
Chen, Shuzhen, et al., "The role of the autonomic nervous system in hypertension: a bond graph model study", Physiological measurement 29.4 (2008): 473, (2008), 473-495.
Clark, Bryan Allen, et al., "Pain Management Based on Functional Measurements", U.S. Appl. No. 62/445,075, filed Jan. 11, 2017.

Davydov, Dmitry M., et al., "Cardiovascular activity and chronic pain severity", Physiology & Behavior 152, 203-216 (2015).
Elgendi, Mohamed, "On the analysis of fingertip photoplethysmogram signals", Current cardiology reviews 8.1, (2012), 14-25.
Fagius, J., et al., "The cold pressor test: effects on sympathetic nerve activity in human muscle and skin nerve fascicles", Acta physiologica Scandinavica 137.3, (1989), 325-334.
Foo, H., et al., "Brainstem modulation of pain during sleep and waking", Sleep medicine reviews 7.2, (2003), 145-154.
Frederiks, Joost, et al., "Within-subject electrocardiographic differences at equal heart rates: role of the autonomic nervous system", Pflügers Archiv 441.5, (2001), 717-724.
Gesche, Heiko, et al., "Continuous blood pressure measurement by using the pulse transit time: comparison to a cuff-based method", European journal of applied physiology 112.1, (2012), 309-315.
Godfrey, A., et al., "Direct measurement of human movement by accelerometry", Medical Engineering & Physics 30 (2008) 1364-1386.
Godfrey, A., et al., "Instrumenting gait with an accelerometer: a system and algorithm examination", Medical Engineering & Physics, Mar. 2015, doi:10.1016/j.medengphy.2015.02.003, 24 pgs.
Hallman, David M., et al., "Long-Term Monitoring of Physical Behavior Reveals Different Cardiac Responses to Physical Activity among Subjects with and without Chronic Neck Pain", BioMed Research International, vol. 2015, Article ID 907482, 11 pages, http://dx.doi.org/10.1155/2015/907482, 11 pages.
Jensen, MP, et al., "Brain EEG activity correlates of chronic pain in persons with spinal cord injury: clinical implications", Nature; Spinal Cord; 51, (Jul. 17, 2012), 55-58.
La Rovere, Maria Teresa, et al., "Baroreflex Sensitivity: Measurement and Clinical Implications", Ann Noninvasive Electrodardiol, 13(2):191-207, 2008.
Littlewort, Gwen C., et al., "Automatic Coding of Facial Expressions Displayed During Posed and Genuine Pain", Image and Vision Computing, 27(12) p. 1741-1844.
Looney, David, et al., "The In-the-Ear Recording Concept", IEEE Pulse Nov./Dec. 2012, 32-42.
McCracken, Lance M., et al., "Disrupted sleep patterns and daily functioning in patients with chronic pain", Pain Res Manage vol. 7 No. 2 Summer 2002 75-79.
Mikkelsen, Kaare B., et al., "EEGRecordedfromtheEar:CharacterizingtheEar-EEGMethod", FrontiersinNeuroscience|www.frontiersin.org, Nov. 2015|vol. 9|Article438, 8 pgs.
Moxham, I.M., "Understanding Arterial Pressure Waveforms", Southern African Journal of Anaesthesia and Analgesia 9.1, (2003), 40-42.
Mukkamala, R., et al., "Toward ubiquitous blood pressure monitoring via pulse transit time: theory and practice", IEEE Transactions on Biomedical Engineering 62.8, (2015), 1879-1901.
Ng, Joseph, et al., "EMG activity of trunk muscles and torque output during isometric axial rotation exertion: a comparison between back pain patients and matched controls", Journal of Orthopaedic Research; 20, (2002), 112-121.
Perruchoud, Christophe, et al., "Assessment of Physical Activity of Patients with Chronic Pain", Neuromodulation: Technology at the Neural Interface; 17, (2012), 42-47.
Pinheiro, Eulália Silva Dos Santos, et al., "Electroencephalographic Patterns in Chronic Pain: A Systematic Review of the Literature", Plos One | DOI:10.1371/journal.pone.0149085 Feb. 25, 2016, 27 pgs.
Poon, C.C.Y., "Cuff-less and noninvasive measurements of arterial blood pressure by pulse transit time", 2005 IEEE Engineering in Medicine and Biology 27th Annual Conference. IEEE, 2006., (2006), 5877-5880.
Prkachin, Kenneth, "The consistency of facial expressions of pain: a comparison across modalities", Pain, 51, (1992), 279-306.
Roy, Sourav Dey, et al., "An Approach for Automatic Pain Detection through Facial Expression", Procedia Computer Science 84 (2016) 99-106.
Sano, Akane, et al., "Quantitative analysis of wrist electrodermal activity during sleep", Int J Psychophysiol. Dec. 2014 ; 94(3), (2014), 382-389.

(56) References Cited

OTHER PUBLICATIONS

Shouldice, R., "PR and PP ECG intervals as indicators of autonomic nervous innervation of the cardiac sinoatrial and atrioventricular nodes", Neural Engineering, 2003. Conference Proceedings. First International IEEE EMBS Conference on. IEEE, (Mar. 2003), 261-264.
Sihvonen, T., et al., "Electric behavior of low back muscles during lumbar pelvic rhythm in low back pain patients and healthy controls", Archives of physical medicine and rehabilitation; 72.13, (1991), 1080-1087.
Srivastava, Kyle Harish, et al., "Pain Management Based on Cardiovascular Parameters", U.S. Appl. No. 62/445,053, filed Jan. 11, 2017.
Srivastava, Kyle Harish, et al., "Pain Management Based on Emotional Expression Measurements", U.S. Appl. No. 62/445,082, filed Jan. 11, 2017.
Thakur, Pramodsingh Hirasingh, et al., "Method and Apparatus for Pain Control Using Baroreflex Sensitivity During Posture Change", U.S. Appl. No. 62/412,587, filed Oct. 25, 2016.
Thakur, Pramodsingh Hirasingh, et al., "Systems and Methods for Closed-Loop Pain Management", U.S. Appl. No. 62/400,313, filed Sep. 27, 2016.
Wu, Hao-Yu, et al., "Eulerian Video Magnification for Revealing Subtle Changes in the World", ACM Transactions on Graphics 31(4), (2012), 1-8.
Zeng, Zhihong, et al., "A Survey of Affect Recognition Methods: Audio, Visual and Spontaneous Expressions", ICMI'07, Nov. 12-15, 2007, 126-133.
Zhou, Jing, et al., "Recurrent Convolutional Neural Network Regression for Continuous Pain Intensity Estimation in Video", arXiv preprint arXiv:1605.00894 (2016) 84-92.
"2015 Sleep in America® Poll Sleep and Pain—Summary of Findings", National Sleep Foundation, (2015), 1-54.
Ahern, David K., et al., "Comparison of lumbar paravertebral EMG patterns in chronic low back pain patients and non-patient controls", Pain, 34, (1988), 153-160.
Allum, John H.J., et al., "A speedy solution for balance and gait analysis: angular velocity measured at the centre of body mass", Current Opinion in Neurology 18, (2005), 15-21.
Alo, Kenneth M., et al., "Effect of Spinal Cord Stimulation on Sensory Nerve Conduction Threshold Functional Measures", Neuromodulation, vol. 3, No. 3, (2000), 145-154.
Annoni, Elizabeth M., et al., "Method and Apparatus for Pain Management Using Objective Pain Measure", U.S. Appl. No. 62/400,336, filed Sep. 27, 2016.
Arsenault, Marianne, et al., "Pain Modulation Induced by Respiration: Phase and Frequency Effects", Neuroscience 252, (2013), 501-511.
Artner, Juraj, et al., "Prevalence of sleep deprivation in patients with chronic neck and back pain: a retrospective evaluation of 1016 patients", Journal of Pain Research: 6, (2013), 1-6.
Bakker, Jorn, et al., "What's your current stress level? Detection of stress patterns from GSR sensor data", Eindhoven University of Technology—The Netherlands, (2011), 1-8.
Baliki, Marwan N., et al., "Beyond Feeling: Chronic Pain hurts the Brain, Disrupting the Default-Mode Network Dynamics", The Journal of Neuroscience, 28 (6), (Feb. 6, 2008), 1398-1403.
Banos, Oresti, et al., "PhysioDroid: Combining Wearable Health Sensors and Mobile Devices for a Ubiquitous, Continuous, and Personal Monitoring", The Scientific World Journal, vol. 2014 Article ID 190824, (2014), 11 pgs.
Barad, Meredith J., et al., "Complex Regional Pain Syndrome Is Associated With Structural Abnormalities in Pain-Related Regions of the Human Brain", The Journal of Pain, vol. 15, No. 2, (Feb. 2914), 197-203.
Barkley, Jacob E., et al., "The effect of spinal cord stimulation unit revision on perceived pain, anxiety, mobility and physical activity in individuals with low back/lower extremity pain", Kent State University—The Spine and Pain Institute, Presented at Annual Meeting of the North American Neuromodulation Society (NANS) on Dec. 11-14, 2014, 1 pg.
Beneck, George J., et al., "Spectral analysis of EMG using intramuscular electrodes reveals non-linear fatigability characteristics in persons with chronic low back pain", Journal of Electromyography and Kinesiology 23, (2013), 70-77.
Ben-Israel, Nir, et al., "Monitoring the nociception level: a multiparameter approach", J Clin Monit Comput, (Jul. 2012), 10 pgs.
Ben-Israel, Nir, et al., "Monitoring the nociception level: a multiparameter approach", J Clin Monit Comput 27, (2013), 659-668.
Boselli, E., et al., "Prediction of immediate postoperative pain using the analgesia/nociception index: a prospective observational study", British Journal of Anaesthesia 112 (4):, (2014), 715-721.
Boselli, E., et al., "Prospective observational study of the non-invasive assessment of immediate postoperative pain using the analgesia/nociception index (ANI)", British Journal of Anaesthesia 111, (2013), 453-459.
Broucqsault-Dédrie, Celine, et al., "Measurement of Heart Rate Variability to Assess Pain in Sedated Critically Ill Patients: A Prospective Observational Study", Plos One, (Jan. 25, 2016), 1-11.
Chan, C. W.Y., et al., "Subjective pain sensation is linearly correlated with the Flexion reflex in man", Brain Research, 479, (1989), 145-150.
Chapman, C. Richard, et al., "Phasic pupil dilation response to noxious stimulation in normal volunteers: relationship to brain evoked potentials and pain report", (1999), 44-52.
Cheng, Qian, et al., "GaitTrack: Health Monitoring of Body Motion from Spatio-Temporal Parameters of Simple Smart Phones", The ACM Conference on Bioinformatics, Computational Biology, Biomed Biomedical Informatics (BCB) Health Information Symposium (HIS), Sep. 25, 2013,, (2013), 1-10.
Chuang, Chiung-Cheng, et al., "Photoplethysmography variability as an alternative approach to obtain heart rate variability information in chronic pain patient", J Clin Monit Comput—Published online, (Feb. 24, 2015), 1-6.
Chung, Ok Y., "Baroreflex sensitivity associated hypoalgesia in healthy states is altered by chronic pain", Pain 138, (2008), 87-97.
Ciampi De Andrade, Daniel, et al., "Neurophysiological assessment of spinal cord stimulation in failed back surgery syndrome", Pain 150, (2010), 485-491.
Cinaz, Burcu, et al., "Monitoring of mental workload levels during an everyday life office-work scenario", Pers Ubiquit Comput 17, (2013), 229-239.
Culic, Ognjen, et al., "Serum activities of adenosine deaminase, dipeptidyl peptidase IV and prolyl endopeptidase in patients with fibromyalgia:diagnostic implications", Clin Rheumatol 35, (2016), 2565-2571.
Dansie, Elizabeth J., et al., "Activity in Adults with Chronic Widespread Pain", The Journal of Pain—Accepted Manuscript, (2014), 33 pgs.
De-La-Herran, Alvaro M., et al., "Gait Analysis Methods: An Overview of Wearable and Non-Wearable Systems, Highlighting Clinical Applications", Sensors 14, (2014), 3362-3394.
Denk, Franziska, et al., "Chronic Pain: Emerging Evidence for the Involvement of Epigenetics", Neuron 73 (3), (2012), 435-444.
Duschek, S., "Relationship between baroreceptor cardiac reflex sensitivity and pain experience in normotensive individuals", International Journal of Psychophysiology 65, (2007), 193-200.
Eisenberg, Elon, et al., "Quantitative Sensory Testing for Spinal Cord Stimulation in Patients With Chronic Neuropathic Pain", (2006), 161-165.
Evans, Subhadr, et al., "Heart rate variability as a biomarker for autonomic nervous system response differences between children with chronic pain and healthy control children", Journal of Pain Research 3.6, (2013), 449-457.
Fazalbhoy, Azharuddin, et al., "Individual differences in the cardiovascular responses to tonic muscle pain: parallel increases or decreases in muscle sympathetic nerve activity, blood pressure and heart rate", Exp Physiol 97.10, (2012), 1084-1092.
Geisser, Michael E., et al., "Pain-Related Fear, Lumbar Flexion, and Dynamic EMG Among Persons With Chronic Musculoskeletal Low Back Pain", Clin J Pain, vol. 20, No. 2, (Apr. 2004).

(56) References Cited

OTHER PUBLICATIONS

Generaal, Ellen, et al., "Reduced hypothalamic-pituitary-adrenal axis activity in chronic multi-site musculoskeletal pain: partly masked by depressive and anxiety disorders", BMC Musculoskeletal Disorders, 15:227, (2014), 1-11.
Gouveia, S., et al., "Assessing Baroreflex Sensitivity in the Sequences Technique: Local versus Global Approach", Computers in Cardiology, 32, (2005), 279-282.
Granovsky, Yelena, et al., "Objective Correlate of Subjective Pain Perception by Contact Heat-Evoked Potentials", The Journal of Pain, vol. 9, No. 1, (Jan. 2008), 53-63.
Green, Alexande L., "Measurement of muscle sympathetic nerve activity reveals true sympathetic changes in chronic pain", Exp Physiol 97.10, (2012), 1083.
Hallman, David, et al., "Autonomic regulation, physical activity and perceived stress in subjects with musculoskeletal pain: 24-hour ambulatory monitoring", International Journal of Psychophysiology 86, (2012), 276-282.
Hallman, David M., et al., "Changes in physical activity and heart rate variability in chronic neck-shoulder pain: monitoring during work and leisure time", Int Arch Occup Environ Health 87, (2014), 735-744.
Hartwich, Doreen, et al., "Effect of muscle metaboreflex activation on spontaneous cardiac baroreflex sensitivity during exercise in humans", J Physiol 589.24, (2011), 6157-6171.
Jess, Gunnar, et al., "Monitoring heart rate variability to assess experimentally induced pain using the analgesia nociception index—A randomised volunteer study", Eur J Anaesthesiol 32, (2015), 1-8.
Kang, Jon-Eun, et al., "Pulse transit time shows vascular changes caused by propofol in children", J Clin Monit Comput 29, (2015), 533-537.
Keefe, Francis J,, et al., "An Objective Approach to Quantifing Pain Behavior and Gait Patterns in Low Back Pain Patients", Pain, 21, (1985), 153-161.
Kemler, Marius A., et al., "Impact of Spinal Cord Stimulation on Sensory Characteristics in Complex Regional Pain Syndrome Type 1—A Randomized Trial", Anesthesiology, 95, (2001), 72-80.
Keshari, Kayvan R., et al., "Lactic Acid and Proteoglycans as Metabolic Markers dor Discogenic Back Pain", Spine, vol. 13, No. 3, (2008), 312-317.
Kim, Young UK, et al., "Pulse Transit Time as a Predictor of the Efficacy of a Celiac Plexus Block in Patients With Chronic Intractable Abdominal Pain", Clin J Pain, vol. 32, No. 6, (Jun. 2015), 522-526.
Kodituwakku, Sandun, et al., "Point Process Respiratory Sinus Arrhythmia Analysis during Deep Tissue Pain Stimulation", Computing in Cardiology 38, (2011), 193-196.
Koenig, J., et al., "Heart rate variability and experimentally induced pain in healthy adults: A systematic review", European Journal of Pain 18, (2014), 301-314.
Koenig, Julian, et al., "Chronic Pain and Heart Rate Variability in a Cross-Sectional Occupational Sample Evidence for Impaired Vagal Control", The Clinical Journal of Pain, Publish Ahead of Print, (2015), 31 pgs.
Lamoth, Claudine J.C., et al., "How do persons with chronic low back pain speed up and slow down? Trunk-pelvis coordination and erector spinae activity during gait", Gait & Posture 23, (2006), 230-239.
Lamoth, Claudine J.C., et al., "Pelvis-Thorax Coordination in the Transverse Plane During Walking in Persons With Nonspecific Low Back Pain", Spine, vol. 27, No. 4, (2002), E92-E99.
Lane, James D., et al., "Respiratory Sinus Arrhythmia and Cardiovascular Responses to Stress", Psychophysiology, vol. 29, No. 4, (1992), 461-470.
Latremoliere, Alban, et al., "Reduction of Neuropathic and Inflammatory Pain through Inhibition of the Tetrahydrobiopterin Pathway", Neuron, 86 (6), (2015), 1393-1406.
Ledowski, Thomas, et al., "The influence of age and sex on the relationship between heart rate variability, haemodynamic variables and subjective measures of acute post-operative pain", European Journal of Anaesthesiology, vol. 28, No. 6, (2011), 433-437.
Lee, Jihyoung, et al., "Validation of normalized pulse volume in the outer ear as a simple measure of sympathetic activity using warm and cold pressor tests: towards applications in ambulatory monitoring", Physiol. Meas. 34, (2013), 359-375.
Lidberg, Lars, et al., "Sympathetic Skin Nerve Dischai gcs in Relation lo Anipliliule ol Skin Resistance Responses", Psychophysiology, vol. 18, No. 3, (May 1981), 268-270.
Logier, R., et al., "PhysioDoloris: a monitoring device for Analgesia / Nociception balance evaluation using Heart Rate Variability analysis", 32nd Annual International Conference of the IEEE EMBS, (2010), 1194-1197.
Marchi, Antonio, et al., "Pain Biomarkers", Clin Drug Invest, 29 Suppl 1, (2009), 41-46.
Martini, Chris H., et al., "Ability of the Nociception Level, a Multiparameter Composite of Autonomic Signals, to Detect Noxious Stimuli during Propofol-Remifentanil Anesthesia", Anesthesiology, vol. 123, No. 3, (2015), 524-534.
Mauer, C,, et al., "Quantitative sensory testing in the German Research Network on Neuropathic Pain (DFNS): Somatosensory abnormalities in 1236 patients with different neuropathic pain syndromes", Pain 150, (2010), 439-450.
McBeth, John, et al., "Hypothalamic-pituitary-adrenal stress axis function and the relationship with chronic widespread pain and its antecedents", [Online]. Retrieved from the Internet: <URL: http://arthritis-research.com/content/7/5/R992, (2005), R992-R1000.
McCarthy, K. F., et al., "Cerebrospinal fluid levels of glial cell-derived neurotrophic factor correlate with spinal cord stimulation frequency in patients with neuropathic pain: a preliminary report", Spinal Cord 52, (2014), S8-S10.
Mironer, Y. Eugene, et al., "Pain Tolerance Threshold: A Pilot Study of an Objective Measurement of Spinal Cord Stimulator Trial Results", Pain Medicine, vol. 1, No. 2, (2000), 110-115.
Moseley, G. Lorimer, et al., "Tactile Discrimination, but not tactile stimulation alone, reduces chronic limg pain", Pain 137, (2008), 600-608.
Mylius, Vett, et al., "Sex differences in nociceptive withdrawal reflex and pain perception", Somatosensory and Motor Research 22 (3), (Sep. 2005), 207-211.
Neblett, Randy, et al., "What Is The Best Surface EMG Measure of Lumbar Flexion-Relation for Distinguishing Chronic Low Back Pain Patients From Pain-Free Controls?", Clin J Pain 29 (4)—NIH Public Access, (Apr. 2013), 334-340.
Palermo, Tonya M., et al., "Subjective Sleep Disturbances in Adolescents With Chronic Pain: Relationship to Daily Functioning and Quality of Life", The Journal of Pain, vol. 6, No. 3, (Mar. 2995), 201-207.
Panjabi, Manohar, "Clinical spinal instability and low back pain", Journal of Electromyography and Kinesiology 13, (2003), 371-379.
Patti, Gary J., et al., "Metabolomics implicates altered sphingolipids in chronic pain of neuropathic origin", nature chemical biology, vol. 8, (Mar. 2012), 232-234.
Plaza-Manzano, Gustavo, et al., "Changes in Biochemical Markers of Pain Perception and Stress Response After Spinal Manipulation", Journal of Orthopaedic & Sports Physical Therapy, vol. 44, No. 4, (Apr. 2014), 231-239.
Pleger, Burkhard, et al., "Patterns of cortical reorginization parallel impaired tactile discrimination and pain intensity in complex regional pain syndrome", NeuroImage 32, (2006), 503-510.
Pluijms, Wouter A., et al., "Increased Contact Heat Evoked Potential Stimulation Latencies in Responders to Spinal Cord Stimulation for Painful Diabetic Cord Stimulation for Painful Diabetic Cord Stimulation for Painful Diabetic Polyneuropathy", Neuromodulation 18, (2015), 126-132.
Prichep, Leslie S., et al., "Evaluation of the Pain Matrix Using EEG Source Localization: A Feasibility Study", Pain Medicine 12, (2011), 1241-1248.
Raminen, Tina, et al., "The Impact of Spinal Cord Stimulation on Sleep Patterns", Neuromodulation 19, (2016), 477-481.

(56) References Cited

OTHER PUBLICATIONS

Rasche, Dirk, et al., "Quantitative Sensory Testing in Patients With Chronic Unilateral Radicular Neuropathic Pain and Active Spinal Cord Stimulation", Neuromodulation, vol. 9, No. 3, (2006), 239-247.

Rhudy, Jamie L., et al., "Defining the nociceptive flexion reflex (NFR) threshold in human participants: A comparison of different scoring criteria", Pain 128, (2007), 244-253.

Sacco, Marcella, et al., "The Relationship Between Blood Pressure and Pain", The Journal of Clinical Hypertension vol. 15, No. 8, (Aug. 2013), 600-605.

Sarnthein, Johannes, et al., "Increased EEG power and slowed dominant frequncy in patients with neurogenic pain", Brain 129, (2005), 55-64.

Sato, Karina L/, et al., "Spinal Cord Stimulation (SCS) Improves Decreased Physical Activity Induced by Nerve Injury", Behavioral Neuroscience, vol. 128, No. 5, (2914), 625-632.

Sawada, Yukihiro, et al., "Normalized pulse volume (NPV) derived photo-plethysmography as a more valid measure of the finger vascular tone", International Journal of Psychophysiology 41, (2001), 1-10.

Sayar, Kemal, et al., "Sleep Quality in Chronic Pain Patients", Can J. Psychiatry, vol. 47, No. 9, (Nov. 2002), 844-848.

Schulman, Joshua J., et al., "Thalamocortical dysrhythmia syndrome: MEG imaging of neuropathic pain", (Jul. 25, 2014), 33-39.

Schulz, Enrico, et al., "Prefrontal Gamma Oscillations Encode Tonic Pain in Humans", Cerebral Cortex 2015, (Mar. 8, 2015), 1-8.

Sesay, Musa, et al., "Responses of Heart Rate Variability to Acute Pain After Minor Spinal Surgery: Optimal Thresholds and Correlation With the Numeric Rating Scale", J Neurosurg Anesthesiol, vol. 00, No. 00, (2014), 1-7.

Siddall, Phillip J., et al., "Magnetic Resonance Spectroscopy Detects Biochemical Changes in the Brain Associated with Chronic Low Back Pain: A Preliminary Report", Anesth Analg 102, (2006), 1164-1168.

Simoes, Mario A., "Feasibility of Wearable Sensors to Determine Gait Parameters", University of South Florida Scholar Commons, (2011), 1-98.

Skljarevski, V., et al., "The nociceptive flexion reflex in humans—review article", Pain, 96, (2002), 3-8.

Smallwood, Rachel F., et al., "Structural Brain Anomalies and Chronic Pain: A Quantitative Meta-Analysis of Gray Matter Volume", The Journal of Pain, vol. 14, No. 7, (Jul. 2013), 663-675.

Staud, Roland, "Heart rate variability as a biomarker of fibromyalgia syndrome", Fut Rheumatol 3 (5)—NIH Public Access, (Oct. 1, 2008), 475-483.

Storm, H., et al., "Skin conductance correlates with perioperative stress", Acta Anaesthesiol Scand 46, (2002), 887-895.

Sturgeon, John A., et al., "Respiratory Sinus Arrhythmia: a Marker of Resilience to Pain Induction", Int.J. Behav. Med. 21, (2014), 961-965.

Swenne, C. A., "Baroreflex sensitivity: mechanisms and measurement", Neth Heart J 21, (2013), 58-60.

Symons, Frank J., et al., "Can Biomarkers Differentiate Pain and No Pain Subgroups of Nonverbal Children with Cerebral Palsy? A Preliminary Investigation Based on Noninvasive Saliva Sampling", Pain Med 16 (2), (2015), 249-256.

Tagliazucchi, Enzo, et al., "Brain resting state is disrupted in chronic back pain patients", Neurosci Lett. 485 (1)—NIH Public Access, (Nov. 12, 2010), 26-31.

Tao, Weijun, et al., "Gait Analysis Using Wearable Sensors", Sensors 12, (2012), 2255-2283.

Tauda, Makoto, et al., "P2X4receptorsandneuropathicpain", Frontiers in Cellular Neuroscience, vol. 7, Article 191, (Oct. 28, 2013), 1-6.

Terkelsen, Astrid J., et al., "Heart Rate Variability in Complex Regional Pain Syndrome during Rest and Mental and Orthostatic Stress", Anesthesiology, vol. 116, No. 1, (Jan. 2012), 133-146.

Thankur, Pramodsingh Hirasingh, et al., "Method and Apparatus for Pain Management Using Heart Sounds", U.S. Appl. No. 62/395,641, filed Sep. 16, 2016.

Theuvenel, Peter J., et al., "Responses to Median and Tbial Nerve Stimulation in Patients with Chronic Neuropathic Pain", Brain Topography, vol. 11, No. 4, (1999), 306-313.

Uceyler, Nuncan, et al., "Differential expression of cytokines in painful and painless neuropathies", (2007).

Uzar, E., et al., "Serum cytokine and pro-brain natriuretic peptide (BNP) levels in patients with migraine", European Review for Medical and Pharmacological Sciences; 15, (2011), 1111-1116.

Van Velzen, Marit H.N., et al., "Effect of heat-induced pain stimuli on pulse transit time and pulse wave amplitude in healthy volunteers", Physiological Measurement 37, (2016), 52-66.

Villarejo, Viqueira Maria, et al., "A Stress Sensor Based on Galvanic Skin Response (GSR) Controlled by ZigBee", Sensors 12, (2012), 6075-6101.

Walton, K. D., et al., "Abnormal thalamocortical activity in patients with Complex Regional Pain Syndrome (CRPS) Type 1", Pain 150, (2010), 41-51.

Willer, Jean Claude, "Comparative Study of Perceived Pain and Nociceptive Flexion Reflex in Man", Pain, 3, (1977), 69-80.

Williams, Dewayne P., et al., "Effects of Chronic Pelvic Pain on Heart Rate Variability in Women", The Journal of Urology, vol. 194,, (Nov. 2015), 1-6.

Wong, Arnold Y.L., et al., "Does experimental low back pain change posteroanterior lumbar spinal stiffness and trunk muscle activity? A randomized crossover study", Clinical Biomechanics 34, (2016), 45-52.

Wong, Jih-Sen, et al., "A comparative study of pulse rate variability and heart rate variability in healthy subjects", J Clin Monit Comput 26, (2012), 107-114.

Zamuner, Antonio R., et al., "Respiratory Sinus Arrhythmia and its Association with Pain in Women with Fibromyalgia Syndrome", Pain Practice, vol. 16, Issue 6, (2016), 704-711.

Zamunér, A. R., et al., "Relationship between sympathetic activity and pain intensity in fibromyalgia", Clin Exp Rheumatol 33—Abstract, [Online]. Retrieved from the Internet: <URL: http://www.ncbi.nlm.nih.gov.ezp3.lib.umn.edu/pubmed/25786044, (Feb. 2015), 1-2.

Zhang, John, "Effect of Chiropractic Care on Heart Rate Variability and Pain in a Multisite Clinical Study", Jimmal of Manipulative and Physiological Therapeutics, vol. 29, No. 4, (2006), 267-274.

Zhou, Jing, et al., "Recurrent Convolutional Neural Network Regression for Continuous Pain Intensity Estimation in Video", Technical Report, (May 3, 2016), 1-11.

U.S. Appl. No. 15/788,403, filed Oct. 19, 2017, Method and Apparatus for Pain Control Using Baroreflex Sensitivity During Posture Change.

SYSTEMS AND METHODS FOR CLOSED-LOOP PAIN MANAGEMENT

CLAIM OF PRIORITY

This application claims the benefit of priority under 35 U.S.C. § 119(e) of U.S. Provisional Patent Application Ser. No. 62/400,313, filed on Sep. 27, 2016, which is herein incorporated by reference in its entirety.

CROSS REFERENCE TO RELATED APPLICATIONS

This application is related to commonly assigned U.S. Provisional Patent Application Ser. No. 62/395,641, entitled "METHOD AND APPARATUS FOR PAIN MANAGEMENT USING HEART SOUNDS", filed on Sep. 16, 2016 and U.S. Provisional Patent Application Ser. No. 62/400,336, entitled "METHOD AND APPARATUS FOR PAIN MANAGEMENT USING OBJECTIVE PAIN MEASURE", filed on Sep. 27, 2016, which are incorporated by reference in their entirety.

TECHNICAL FIELD

This document relates generally to medical systems and more particularly to systems, devices, and methods for pain management.

BACKGROUND

Neuromodulation, also referred to as neurostimulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). Implantable neuromodulation systems have been applied to deliver such a therapy. An implantable neuromodulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

SCS, by way of example and not limitation, has been used to treat chronic pain syndromes. Some neural targets may be complex structures with different types of nerve fibers. An example of such a complex structure is the neuronal elements in and around the spinal cord targeted by SCS.

SUMMARY

Pain therapy, such as provided by SCS, may be delivered according to a degree of pain perceived by the patient. The degree of pain may be subjectively provided, such as based on patient report of severity, pattern, or duration of pain sensation. Using the patient reported pain sensation, a clinician may manually program a neuromodulator for delivering pain therapy. However, the subjective description of pain sensation may have inter-patient variation. It may also have intra-patient variation, such as due to progression of a chronic disease, or change in general health status or medication. Having a patient provide pain description for each pain episode may not be efficient in timely pain treatment. Additionally, manual programming of pain therapy by a clinician may be difficult for patients in an ambulatory setting, such as when a patient needs therapy adjustment but lacks immediate professional medical assistance. The present inventors have recognized that there remains a demand for improving pain management, such as via an automated closed-loop pain therapy system based at least on objective pain assessment.

Example 1 is a system for managing pain in a patient. The system may comprise two or more sensors configured to respectively sense two or more signals from the patient where the signals include physiological or functional signals, a pain analyzer coupled to the two or more sensors, and an output unit. The pain analyzer may be configured to generate a plurality of signal metrics from the sensed two or more signals and a plurality of weight factors corresponding to the plurality of signal metrics. The weight factors indicate the corresponding signal metrics reliability in representing an intensity of the pain. The pain analyzer may generate a pain score using the plurality of signal metrics and the plurality of weight factors. The output unit may be configured to output the pain score to a user or a process.

In Example 2, the subject matter of Example 1 optionally includes an electrostimulator and a controller. The electrostimulator may be configured to generate electrostimulation energy to treat pain. The controller may be configured to control the electrostimulator to deliver a pain therapy, including controlling the electrostimulation energy generated by the electrostimulator according to the pain score.

In Example 3, the subject matter of Example 2 optionally includes the electrostimulator that may be configured to deliver spinal cord stimulation (SCS) via one or more electrodes positioned at a target site on or near a spinal cord of the patient.

In Example 4, the subject matter of Example 2 optionally include the controller that may be configured to deliver first electrostimulation to the patient in response to the pain score exceeding a threshold, and to deliver second electrostimulation to the patient in response to the pain score falling below a threshold. The first and second electrostimulations may differ in at least one of electrostimulation energy, pulse shape, or electrostimulation pattern.

In Example 5, the subject matter of any one or more of Examples 1-4 optionally include the two or more sensors configured to respectively sense the physiological or functional signals. The physiological signals may be selected from the group of signals consisting of: a heart rate signal; a heart rate variability signal; a heart sounds signal; a thoracic impedance signal; a respiration signal; and one or more biochemical signals or signals of biomarker expression levels. The functional signals may be selected from the group consisting of: a posture; a gait; a balance indicator; and a physical activity.

In Example 6, the subject matter of any one or more of Examples 1-5 optionally include the pain analyzer that may include a weight generator configured to: compute correlations between a plurality of quantified pain scales and measurements of the plurality of signal metrics corresponding to the plurality of quantified pain scales; and determine or adjust the weight factors to be proportional to the correlations. The pain analyzer may be configured to generate the pain score using a linear or nonlinear combination of the plurality of the signal metrics respectively weighted by the plurality of weight factors.

In Example 7, the subject matter of Example 6 optionally includes a memory configured to store the plurality of quantified pain scales including quantification of one or more historical pain episodes. The weight generator may be configured to determine the correlations between (1) the quantification of the one or more historical pain episodes and (2) the plurality of signal metrics measured during the one or more historical pain episodes.

In Example 8, the subject matter of any one or more of Examples 6-7 optionally include a user interface configured to receive user input of the plurality of quantified pain scales in response to programmed electrostimulation that includes one or more pain episodes. The weight generator may be configured to determine the correlations between (1) the user input of the plurality of quantified pain scales and (2) the plurality of signal metrics measured during the one or more induced pain episodes.

In Example 9, the subject matter of Example 8 optionally includes the weight generator that may be configured to interpolate or extrapolate the user input of the plurality of pain scales and the corresponding measurements of the plurality of signal metrics; and determine the correlations between (1) the interpolated or extrapolated pain scales and (2) the interpolated or extrapolated signal metrics measurements corresponding to the interpolated or extrapolated pain scales.

In Example 10, the subject matter of any one or more of Examples 6-9 optionally include the pain analyzer that may be configured to determine or adjust the respective weight factors further based on patient demographic information.

In Example 11, the subject matter of any one or more of Examples 6-10 optionally include the pain analyzer that may be configured to determine, for the plurality of signal metrics, respective signal sensitivity to pain, and determine or adjust the respective weight factors further using the signal sensitivity to pain. The signal sensitivity to pain may include a rate of change of the signal metrics over time during a pain episode.

In Example 12, the subject matter of Example 11 optionally includes the pain analyzer that may be configured to generate the pain score using a combination of comparisons between the plurality of the signal metrics and respective threshold values. The threshold values may be proportional to the signal sensitivity to pain.

In Example 13, the subject matter of claim 6 optionally includes the pain analyzer that may be configured to generate a projection vector using (1) a first covariance matrix of first plurality of signal metrics generated from the functional or physiological signals sensed during a historical or induced pain episode with a first pain scale and (2) a second covariance matrix of second plurality of the signal metric generated from the functional or physiological signals sensed during a historical or induced pain episode with a second pain scale, and generate the pain score including a projection of the sensed plurality of the signal metrics along a direction of the projection vector.

In Example 14, the subject matter of any one or more of Examples 1-13 optionally includes the pain analyzer that may be configured to differentiate chronic pain from acute pain based on an abruptness of signal metric change over a specified time period.

In Example 15, the subject matter of any one or more of Examples 6-14 optionally include an implantable neuromodulator device (IND) and an external system communicatively coupled to the IND. The IND may include at least a portion of the pain analyzer, the electrostimulator, and sensor circuits coupled to the two or more sensors. The external system may include the weight generator and a programmer configured to program the electrostimulator including programming the pain therapy according to the pain score.

Example 16 is a method for managing pain in a patient using an implantable neuromodulator device (IND). The method comprises sensing two more signals from the patient via two or more sensors where the signals include physiological or functional signals; generating a plurality of signal metrics from the sensed physiological or functional signals; generating a plurality of weight factors corresponding to the plurality of signal metrics, the weight factors indicating the corresponding signal metrics' reliability in representing an intensity of the pain; generate a pain score using the plurality of signal metrics and the plurality of weight factors; delivering a pain therapy via the IND, the pain therapy including electrostimulation energy determined according to the pain score.

In Example 17, the subject matter of Example 16 optionally includes the pain therapy that may include spinal cord stimulation (SCS) of a target site on or near a spinal cord of the patient.

In Example 18, the subject matter of Example 16 optionally includes the determination of the electrostimulation energy includes increasing the electrostimulation energy in response to the pain score exceeding a threshold, or decreasing the electrostimulation energy in response to the pain score falling below a threshold.

In Example 19, the subject matter of Example 16 optionally includes generating a plurality of weight factors including computing correlations between a plurality of quantified pain scales and measurements of the plurality of signal metrics corresponding to the plurality of quantified pain scales; and determining or adjusting the weight factors to be proportional to the correlations; wherein generating the pain score includes computing a linear or nonlinear combination of the plurality of the signal metrics respectively weighted by the plurality of weight factors.

In Example 20, the subject matter of Example 19 optionally includes the correlations computed between (1) quantification of the one or more historical pain episodes and (2) the plurality of signal metrics measured during the one or more historical pain episodes.

In Example 21, the subject matter of claim 19 optionally includes delivering programmed electrostimulation energy via the IND to induce one or more pain episodes; receiving user input of the plurality of quantified pain scales in response to the induced one or more pain episodes; and measuring a plurality of signal metrics during the one or more induced pain episodes. The correlations may be computed between the received user input of the pain scales and the measured plurality of signal metrics.

In Example 22, the subject matter of Example 9 optionally includes generating a projection vector using (1) a first covariance matrix of first plurality of signal metrics generated from the functional or physiological signals sensed during a historical or induced pain episode with a first pain scale and (2) a second covariance matrix of second plurality of the signal metric generated from the functional or physiological signals sensed during a historical or induced pain episode with a second pain scale. Generating the pain score may include computing a projection of the sensed plurality of the signal metrics along a direction of the projection vector.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Advancements in neuroscience and neurostimulation research have led to a demand for using complex and/or individually optimized patterns of neurostimulation energy for various types of therapies. The capability of a neurostimulation system in pain management will be affected by timely detection and accurate quantification of pain such as severity, intensity, duration of pain, or temporal pattern (e.g., persistence) of the pain, or anatomical location and spatial distribution of the pain. Disclosed herein are systems, devices, and methods for programming neurostimulation based on a multi-sensor indicated pain score that is generated using physiological or functional acquired by multiple sensors. In various embodiments, the present system may include a neurostimulator that can adaptively control the delivery of pain therapy by automatically adjusting stimulation parameters based on the multi-sensor indicated pain score. The method of generating the multi-sensor indicated pain score may be updated periodically or in a command mode to account for changes in patient health status.

The present system may be implemented using a combination of hardware and software designed to provide a closed-loop pain management regime to increase therapeutic efficacy, increase patient satisfaction for neurostimulation therapies, reduce side effects, and/or increase device longevity. The present system may be applied in any neurostimulation (neuromodulation) therapies, including but not limited to SCS, DBS, PNS, FES, and Vagus Nerve Stimulation (VNS) therapies. In various examples, instead of providing closed-loop pain therapies, the systems, devices, and methods described herein may be used to monitor the patient and assess pain that either occurs intrinsically or is induced by nerve block procedures or radiofrequency ablation therapies, among others. The patient monitoring may include generating recommendations to the patient or a clinician regarding pain treatment.

Figure 1:
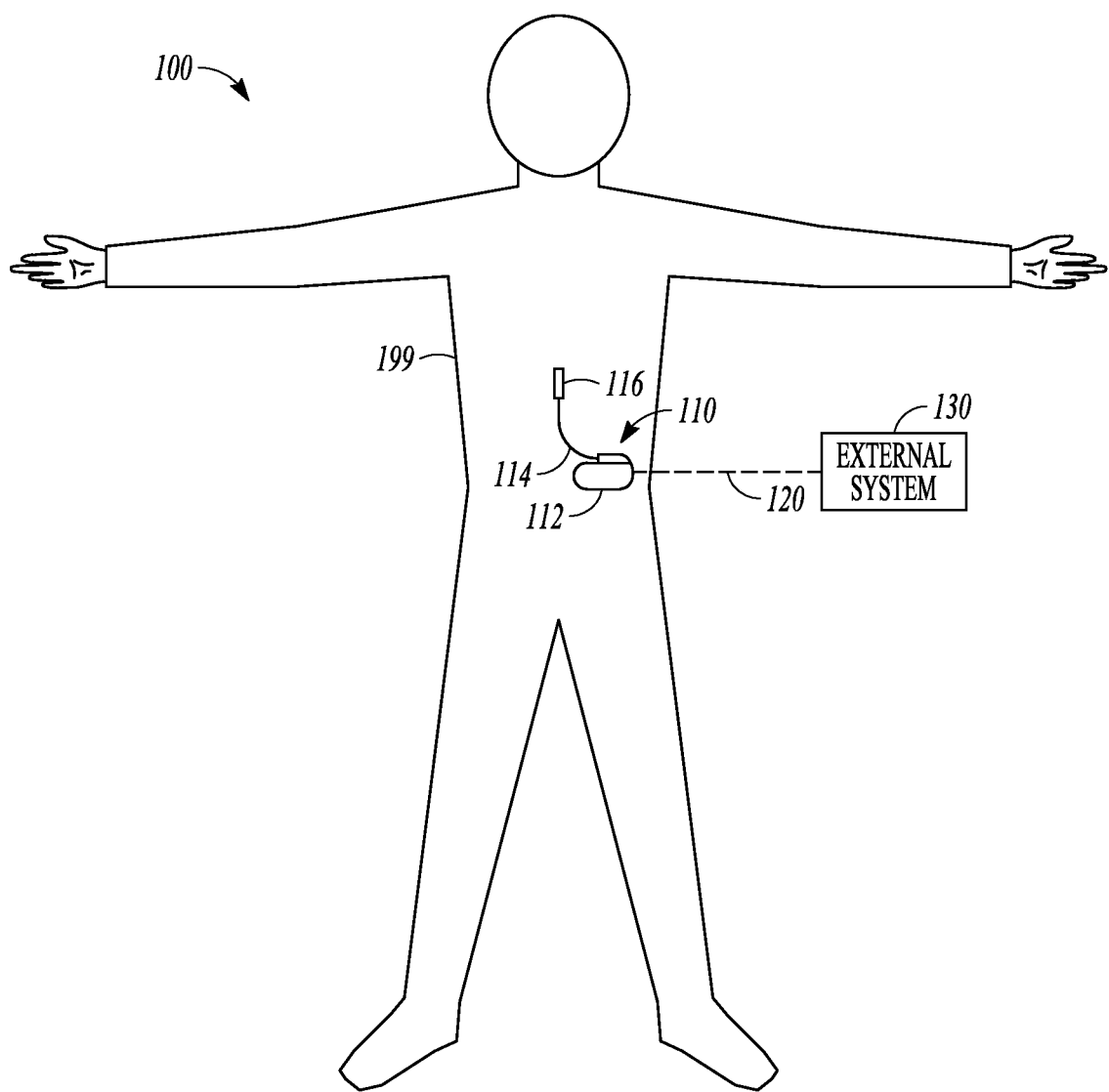
FIG. 1 illustrates, by way of example and not limitation, an example of a neuromodulation system and portions of an environment in which the neuromodulation system may operate.

FIG. 1 illustrates, by way of example and not limitation, an example of a neuromodulation system 100 and portions of an environment in which the neuromodulation system 100 may operate. The neuromodulation system 100 may include an implantable system 110 that may be associated with a body 199 of a patient, and an external system 130. The system 100 may include a communication link 120 providing for communication between the implantable system 110 and the external system 130.

The implantable system 110 may include an ambulatory medical device (AMD), such as an implantable neuromodulator device (IND) 112, a lead system 114, and one or more electrodes 116. The IND 112 may be configured to generate one or more energy modalities or modifying agents for delivery to target tissues for medical diagnosis, or to achieve desired therapeutic effects such as to modify, restore, or improve neural function. Examples of the energy modalities may include electrical, magnetic, or other forms of energy. Examples of the modifying agents may include pain medication such as morphine sulfate, or ziconotide, among others.

In an example, the IND 112 may include a hermetically sealed can, which houses sensing circuitry, electrostimulation circuitry, control circuitry, communication circuitry, a battery, among other components. The sensing circuitry of the IND 112 may be configured to sense physiological or functional signals from the patient via sensing electrodes or various types of ambulatory sensors associated with the patient. In some examples, the sensing electrodes or the ambulatory sensors may be included within the IND 112. The physiological or functional signals may be measured during a pain episode. The physiological or functional signals may be correlated with severity of the pain, and may be used to quantify the pain symptom or to assess efficacy of a pain therapy such as a SCS therapy. The electrostimulation circuitry may generate electrostimulation pulses to stimulate a neural target via the electrodes 116 operably connected to the IND 112. In an example, the electrodes 116 may be positioned on or near a spinal cord, and the electrostimulation circuitry may be configured to deliver SCS to treat pain or other disorders. In another example, the electrodes 116 may be surgically placed at other neural targets such as a brain or a peripheral neutral tissue, and the electrostimulation circuitry may be configured to deliver brain or peripheral stimulation to treat epilepsy, chronic pain, obsessive compulsive disorder, tremor, Parkinson's disease, or dystonia, among other movement and affective disorders.

In various examples, the electrodes 116 may be distributed in one or more leads of the lead system 114 electrically coupled to the IND 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IND 112 and tissue of the patient. The neurostimulation pulses are each delivered from the IND 112 through a set of electrodes selected from the electrodes 116. In various examples, the neurostimulation pulses may include one or more individually defined pulses, and the set of electrodes may be individually definable by the user for each of the individually defined pulses.

Although the discussion herein with respect to the neuromodulation system 100 focuses on implantable device such as the IND 110, this is meant only by way of example and not limitation. It is within the contemplation of the inventors and within the scope of this document, that the systems, devices, and methods discussed herein may also be used for pain management via subcutaneous medical devices, wearable medical devices, or other external medical devices, or a combination of implantable, wearable, or other external devices.

The external system 130 may be communicated with the IND 112 via a communication link 120. The external system 130 may include a dedicated hardware/software system such as a programmer, a remote server-based patient management system, or alternatively a system defined predominantly by software running on a standard personal computer. The external system 130 may control the operation of the IND 112, such as to be configured to program the IND 112 for delivering neuromodulation therapies. The external system 130 may additionally receive via the communication link 120 information acquired by IND 112, such as one or more physiological or functional signals. In an example, the external system 130 may determine a pain score based on the physiological or functional signals received from the IND 112, and program the IND 112 to deliver pain therapy in a closed-loop fashion. Examples of the external system and neurostimulation based on pain score are discussed below, such as with reference to FIGS. 2A-B.

The communication link 120 may include one or more communication channels and intermediate devices between the external system and the IND, such as a wired link, a telecommunication link such as an internet connection, or a wireless link such as one or more of an inductive telemetry link, a radio-frequency telemetry link. The communication link 120 may provide for data transmission between the IND 110 and the external system 130. The transmitted data may include, for example, real-time physiological data acquired by the IND 110, physiological data acquired by and stored in the IND 110, therapy history data, data indicating device operational status of the IND 110, one or more programming instructions to the IND 110 which may include configurations for sensing physiologic signal or stimulation commands and stimulation parameters, or device self-diagnostic test, among others. In some examples, the IND 110 may be coupled to the external system 130 further via an intermediate control device, such as a handheld external remote control device to remotely instruct the IND 110 to generate electrical stimulation pulses in accordance with selected stimulation parameters produced by the external system 130.

Portions of the IND 110 or the external system 130 may be implemented using hardware, software, firmware, or combinations thereof. Portions of the IND 110 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2A:
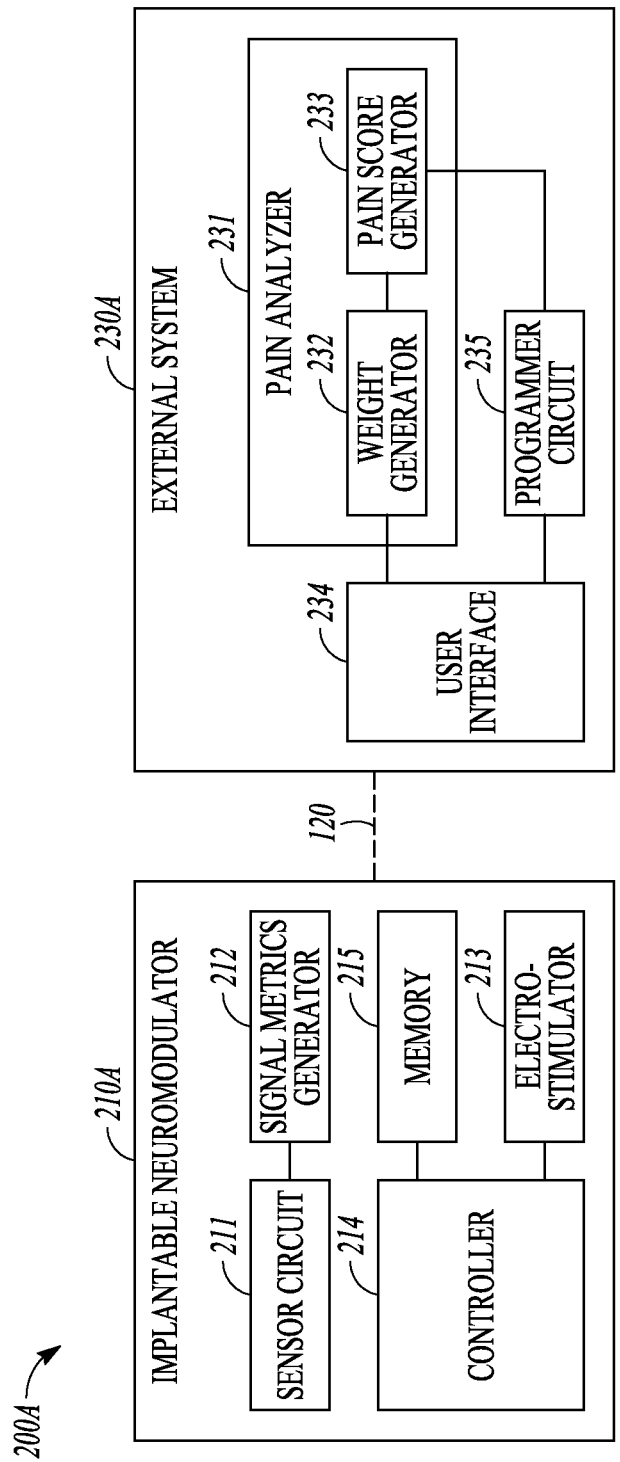
FIGS. 2A-B illustrate, by way of example and not limitation, various embodiments of a pain management system.
Figure 2B:
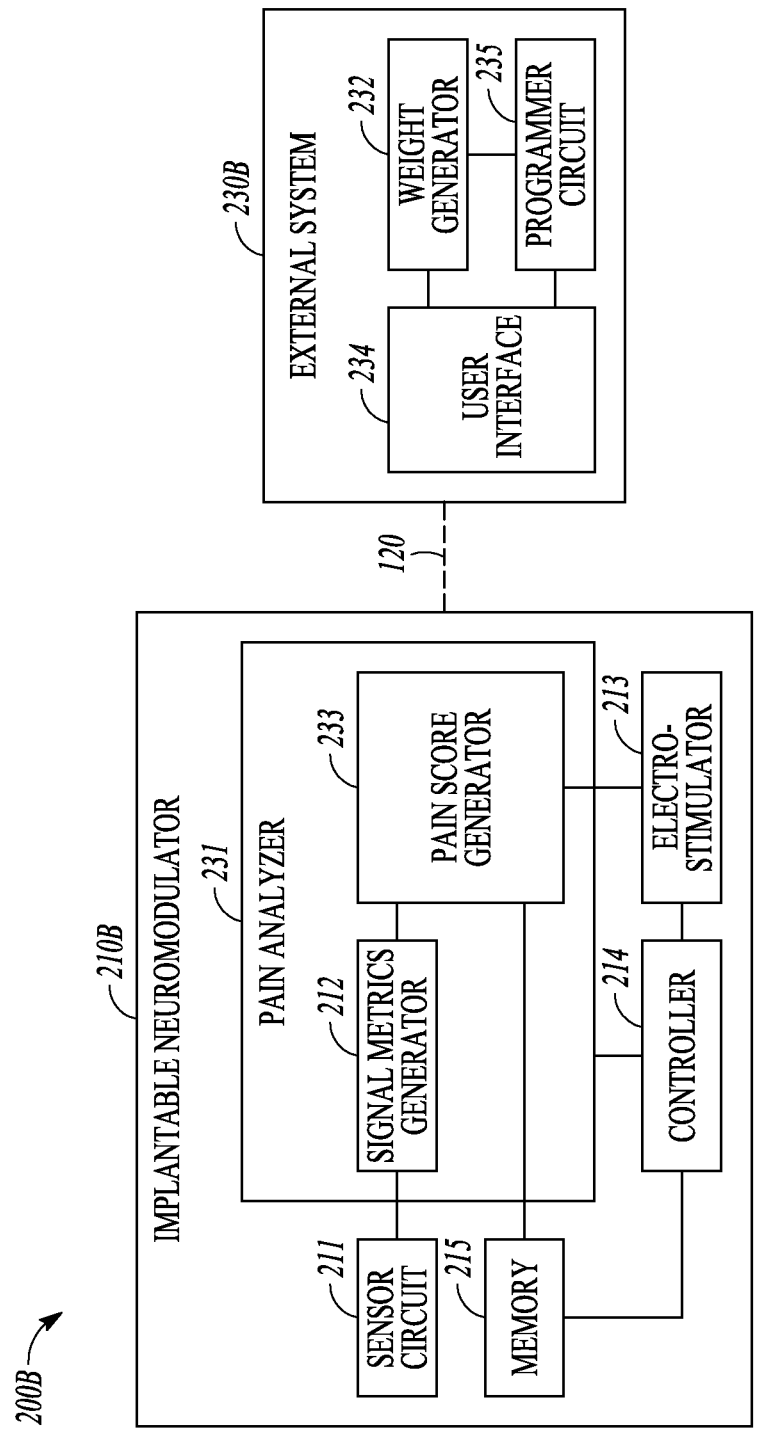

FIGS. 2A-B illustrate, by way of example and not limitation, various examples of a pain management system, which may be an embodiment of the neuromodulation system 100. As illustrated in FIG. 2A, a pain management system 200A may include an implantable neuromodulator 210A and an external system 230A, which are embodiments of the IND 110 and the external system 130, respectively. The external monitor and programmer 231 may be communicatively coupled to the implantable neuromodulator 210A via the communication link 120.

The implantable neuromodulator 210A may include one or more of a sensor circuit 211, a signal metrics generator 212, an electrostimulator 213, a controller 214, and a memory 215. The sensor circuit 211 may be coupled to electrodes or various types of ambulatory sensors associated with the patient, and sense two or more signals from the patient. The signals may include physiological or functional signals. In various examples, the sensor circuit 211 may sense various combinations of physiological or functional signals, which may include at least two physiological signals, at least two functional signals, or a combination of at least one physiological signal and at least one functional signal. The physiological or functional signals, or a combination of physiological and functional signals may be used to quantify the pain symptom.

Various physiological signals, such as cardiac, pulmonary, neural, or biochemical signals may demonstrate characteristic signal properties in response to an onset, intensity, severity, duration, or patterns of pain. In an example, the sensor circuit 211 may sense cardiac signals such as electrocardiograph (ECG) or intracardiac electrogram, heart rate signal, heart rate variability signal, cardiovascular pressure signal, a skin conductivity signal, or heart sounds signal, among others. In another example, the sensor circuit 211 may sense pulmonary signals such as a respiratory signal, a thoracic impedance signal, or a respiratory sounds signal. In still another example, the sensor circuit 211 may sense biochemical signals such as blood chemistry measurements or expression levels of one or more biomarkers, which may include, by way of example and not limitation, B-type natriuretic peptide (BNP) or N-terminal pro b-type natriuretic peptide (NT-proBNP), serum cytokine profiles, P2X4 receptor expression levels, gamma-aminobutyric acid (GABA) levels, TNFα and other inflammatory markers, cortisol, adenosine, Glial cell-derived neurotrophic factor (GDNF), Nav 1.3, Nav 1.7, or Tetrahydrobiopterin (BH4) levels, among other biomarkers.

The sensor circuit 211 may additionally or alternatively sense functional signals including, but not limited to, patient posture, gait, balance, or physical activity signals, among others. In an example, the sensor circuit 211 may be coupled to a wearable or implantable accelerometer to detect an activity intensity or activity duration. The accelerometer may be single-axis or multi-axis accelerometer, and may sense an acceleration signal of at least a portion of a subject's body. The strength of the acceleration signal may be indicative of the physical activity level. In another example, the sensor circuit 211 may be coupled to a wearable or implantable posture sensor to detect a posture or position of the patient. Examples of the posture sensor may include a tilt switch, a single axis accelerometer, or a multi-axis accelerometer, among others. The posture sensor may be disposed external to the body or implanted inside the body. Posture may be represented by, for example, a tilt angle. In some examples, posture or physical activity information may be derived from thoracic impedance information. In yet another example, the sensor circuit 211 may be coupled to wearable sensors, motion sensors that are worn or attached to various parts of the patient's body, such as the foot and waist. Examples of the gait sensors may include accelerometer, gyroscope, magnetoresistive sensors, inclinometers, goniometers, electromagnetic tracking system (ETS), sensing fabric, force sensor, strain gauges, and sensors for electromyography (EMG). Based on these sensors, a single type or a combined sensor system of multiple types of sensors may be used to measure various characteristics of the human gait.

Patient sleep state and information about time of the day may also be related to pain sensation. In an example, the sensor circuit 211 may detect a sleep or awake state of the patient. The sensor circuit 211 may be coupled to one or more accelerometer, piezoelectric sensor, biopotential electrodes and sensors, or other physiologic sensors to detect the posture, change of posture, activity, respiration, heart rate, electroencephalograms, or other signals indicative of a sleep or awake state. In another example, the implantable neuromodulator 210A may include a timing/clock circuit to indicate time of the day when a sensor indicated pain episode occurs.

The signal metrics generator 212 may generate a plurality of signal metrics from the sensed physiological or functional signals. The signal metrics may include statistical parameters extracted from the sensed physiological signal, such as signal mean, median, or other central tendency measures or a histogram of the signal intensity, among others. The signal metrics may additionally or alternatively include morphological parameters such as maximum or minimum within a specified time period such as a cardiac cycle, positive or negative slope or higher order statistics, or signal power spectral density at a specified frequency range, among other morphological parameters. The signal metrics may additionally include timing information such as a time interval between a first characteristic point in one signal and a second characteristic point in another signal. In an example, impedance metrics, which may be extracted from a thoracic or cardiac impedance signal, may include thoracic impedance magnitude within a specified frequency range obtained from. In an example, HS metrics may include intensities of first (S1), second (S2), third (S3), or fourth (S4) heart sound components or a relative intensity such as a ratio between two heart sound components. The signal metrics may additionally or alternatively include electromechanical metrics such as timings of one of the S1, S2, S3, or S4 heart sound components relative to a fiducial point such as a P wave, Q wave, or R wave in an ECG. Such timing information may be indicative of electromechanical coupling of the heart, and may include pre-ejection period (PEP), a systolic timing interval (STI), or a diastolic timing interval (DTI), among other cardiac timing intervals. In an example, respiratory metric may include a respiratory rate, a tidal volume, or a rapid-shallow breathing index (RSBI) computed as a ratio of a respiratory rate measurement to a tidal volume measurement. In another example, physical activity metrics may include physical activity intensity, or a time duration when the activity intensity is within a specified range or above a specified threshold. In yet another example, a blood pressure metrics may include systolic blood pressure, diastolic blood pressure, mean arterial pressure, and the timing metrics of these pressure measurements with respect to a fiducial point.

The signal metrics, optionally along with the physiological or functional signals sensed from the sensor circuit 211, may be transmitted to the external system 230A for pain quantification. The implantable neuromodulator 210A may include a communication circuit that enables data communication between the implantable neuromodulator 210A and the external system 230 via the communication link 120.

The electrostimulator 213 may be configured to generate electrostimulation energy to treat pain. In an example, the electrostimulator 213 may deliver spinal cord stimulation (SCS) via electrodes electrically coupled to the electrostimulator 213. The electrodes may be surgically placed at a region at or near a spinal cord tissue, which may include, by way of example and not limitation, dorsal column, dorsal horn, spinal nerve roots such as the dorsal nerve root, and dorsal root ganglia. The SCS may be in a form of stimulation pulses that are characterized by pulse amplitude, pulse width, stimulation frequency, duration, on-off cycle, pulse shape or waveform, temporal pattern of the stimulation, among other stimulation parameters. Examples of the stimulation pattern may include burst stimulation with substantially identical inter-pulse intervals, or ramp stimulation with incremental inter-pulse intervals or with decremental inter-pulse intervals. In some examples, the frequency or the pulse width may change from pulse to pulse. The electrostimulator 213 may additionally or alternatively deliver electrostimulation to other target tissues such as peripheral nerves tissues. In an example, the electrostimulator 213 may deliver transcutaneous electrical nerve stimulation (TENS) via detachable electrodes that are affixed to the skin. Other non-limiting examples of the electrostimulation delivered by the electrostimulator 213 may include dorsal root ganglia (DRG) stimulation, DBS, motor cortex stimulation (MCS), transcranial direct current stimulation (tDCS), transcutaneous spinal direct current stimulation (tsDCS), trigeminal nerve stimulation, occipital nerve stimulation, VNS, sacral nerve stimulation, pudendal nerve stimulation, sphenopalatine ganglion stimulation, sympathetic nerve modulation, multifidus muscle stimulation, adrenal gland modulation, carotid baroreceptor stimulation, transcranial magnetic stimulation (TMS), tibial nerve stimulation, radiofrequency ablation (RFA), pulsed radiofrequency ablation, ultrasound therapy, high-intensity focused ultrasound (HIFU), optical stimulation, optogenetic therapy, magnetic stimulation, other peripheral tissue stimulation therapies, or other peripheral tissue denervation therapies.

The controller 214, coupled to the electrostimulator 213, may control the generation and delivery of the neurostimulation energy. The controller 214 may control the generation of electrostimulation pulses according to specified stimulation parameters. The stimulation parameters may be provided by a system user. Alternatively, the stimulation parameters may be automatically determined based on the intensity, severity, duration, or pattern of pain, which may be subjectively described by the patient or automatically quantified based on the physiological or functional signals sensed by the sensor circuit 211. For example, when a patient-described or sensor-indicated quantification exceeds a respective threshold value or falls within a specified range indicating elevated pain, the electrostimulation energy may be increased to provide stronger pain relief. Increased electrostimulation energy may be achieved by programming a higher pulse intensity, a higher frequency, or a longer stimulation duration or "on" cycle, among others. Conversely, when a patient-described or sensor-indicated pain quantification falls below a respective threshold value or falls within a specified range indicating no pain or mild pain, the electrostimulation energy may be decreased. The controller 214 may also adjust stimulation parameters to alleviate side effects introduced by the electrostimulation of the target tissue.

Additionally or alternatively, the controller 214 may control the electrostimulator 213 to deliver electrostimulation pulses via specified electrodes. In an example of pain management via SCS, a plurality of segmented electrodes, such as the electrodes 116, may be distributed in one or more leads. The controller 214 may configure the electrostimulator 213 to deliver electrostimulation pulses via a set of electrodes selected from the plurality of electrodes. The electrodes may be manually selected by a system user, or automatically selected based on pain intensity, size and anatomical area of the pain, pain persistence, or pain pattern that are subjectively provided by the patient by automatically assessed based on the physiological or functional signals sensed by the sensor circuit 221.

The implantable neuromodulator 210A may receive the information about electrostimulation parameters and the electrode configuration from the external system 230A via the communication link 120. Additional parameters associated with operation of the electrostimulator 213, such as battery status, lead impedance and integrity, or device diagnostic of the implantable neuromodulator 210A, may be transmitted to the external system 230A. The controller 214 may control the generation and delivery of electrostimulation using the information about electrostimulation parameters and the electrode configuration from the external system 230A. In an example, the controller 214 may control the generation and delivery of electrostimulation in a closed-loop fashion by adaptively adjusting one or more stimulation parameters or stimulation electrode configuration based on the detected signal metrics in response to the pain. The parameter adjustment or stimulation electrode configuration may be executed continuously, periodically at specified time, duration, or frequency, or in a commanded mode upon receiving from a system user a command or confirmation of parameter adjustment.

The implantable neuromodulator 210A may include a memory 215 that stores information about patient physiological or functional responses to pain in patient history. In an example, the memory 215 may store a patient's description or automatically generated quantification of pain from patient's historical pain episodes, and the physiological or functional signals or the signal metrics that are measured during the one or more historical pain episodes. The stored pain quantification and the corresponding signal metrics measurements may be transmitted to the external system 230A, such as via the communication link 120, to evaluate a correlation between the signal metrics and the pain quantification, as to be discussed in the following with respect to the weight generator 232 in the external system 230A.

In some examples, the implantable neuromodulator 210A may include a therapy unit that may be configured to deliver pain therapy other than electrostimulation. Examples of such a therapy unit may include a drug delivery system, such as an intrathecal drug delivery pump that may be surgically placed under the skin and programmed to deliver medication through a catheter to the area around the spinal cord. Other examples of drug delivery system may include a computerized patient-controlled analgesia pump that may deliver the prescribed pain medication to the patient such as via an intravenous line. The controller 214 may be coupled to the pain delivery system to control the therapy dosage according to the pain score. In some examples, both the electrostimulator and the drug delivery pump may be included in the implantable neuromodulator 210A.

The external system 230A may include a pain analyzer 231, a user interface 234, and a programmer circuit 235. The pain analyzer 231 may generate a multi-sensor indicated pain score based on the physiological or functional signals received from the sensor circuit 211. The pain analyzer 231 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The pain analyzer 231 may include circuit sets comprising one or more other circuits or sub-circuits that may, alone or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2A, the pain analyzer 231 may include a weight generator 232 and a pain score generator 233. The weighing generator 232 may generate a plurality of weight factors respectively for the signal metrics. The weight factors may indicate the signal metrics' reliability in representing an intensity of the pain. A sensor metric that is more reliable, or more sensitive or specific to the pain, would be assigned a larger weight than another sensor metric that is less reliable, or less sensitive or specific to the pain.

In an example, the weight generator 232 may include a correlator that can compute correlations between a plurality of (such as N) quantified pain scales P={P(1), P(2), ..., P(N)} and measurements of a signal metric Xa={Xa(1), Xa(2), ..., Xa(N)} corresponding to the N quantified pain scales. The pain scale, such as P(k), may have a numerical or categorical value indicating severity of the pain symptom. The corresponding signal metric measurement Xa(k) may be generated from a physiological or functional signal sensed during a pain episode or a portion of a pain episode with a quantified pain scale of P(k). The correlation Corr(P, Xa) between P and Xa, measured at different quantified pain scales such as an entirety or a portion of {P(1), P(2), ..., P(N)}, may quantitatively indicate the reliability of the signal metric Xa in characterizing the pain. The correlator may similarly correlate P with other signal metrics (such as Xb, Xc, etc.) that are measured during one or more pain episodes having the quantified pain scales of {P(1), P(2), ..., P(N)}, resulting in corresponding correlations such as Corr(P, Xb), Corr(P, Xc), etc.

The weight generator 232 may determine the weight factors for the signal metrics using the respective correlations. In an example, the weight factors may be proportional to the correlations, such that a signal metric having a higher correlation with the pain scales P may be assigned a higher weight factor than a signal metric having a lower correlation with the pain scales P. The pain scales P may be based on quantification of one or more historical pain episodes. Additionally or alternatively, one or more pain episodes may be induced such as by delivering or withholding programmed electrostimulation, or by nerve block procedures or pharmaceutical dose adjustment. The patient may provide pain description via the user interface 234 during the induced pain episodes, and the pain description may be transformed to pain scales P for use by the weight generator 232. In some examples, signal metric reliability may be characterized by variation of multiple measurements of the signal metric measured at a given plain level. A more variable signal metric (e.g., variation of the signal metric measurements exceeding a threshold) is less reliable, and a smaller weight factor may be assigned to the signal metric accordingly. Examples of weight generator for generating respective weight factors for the signal metrics are discussed below, such as with reference to FIGS. 4A-D and FIG. 5.

The pain score generator 233 may be communicatively coupled to the signal metrics generator 212 to receive, via the communication link 120, the signal metrics such as generated during a pain episode. The pain score generator 233 may generate a multi-sensor indicated pain score using the measurements of the signal metrics, and the weight factors such as generated by the weight generator 232. The multi-sensor indicated pain score can be represented as a numerical or categorical value that quantifies the patient's overall pain symptom. In an example, a composite signal metric may be generated using a linear or nonlinear combination of the plurality of the signal metrics respectively weighted by the plurality of weight factors. The pain score generator 233 may compare the composite signal metric to one or more threshold values or range values, and assign a corresponding pain score (such as numerical values from 0 to 10) based on the comparison. In another example, the pain score generator 233 may compare each of the signal metrics to respectively specified threshold or range values, assign a corresponding signal metric-specific pain score, and compute the multi-sensor pain score using a linear or nonlinear fusion of the signal metric-specific pain scores each weighted by their respective weight factors. Examples of the fusion algorithm may include weighted averages, voting, decision trees, or neural networks, among others. The multi-sensor indicated pain score generated by the pain score generator 233 may be output to a system user or a process.

In an example, the pain score generator 233 may generate the multi-sensor indicated pain score using a subset of the signal metrics selected based on the signal metric's temporal pain response profile. For example, some signal metrics, such as heart rate, respiration rate, or galvanic skin response (GSR), may show a quick pain response with a short transient state before reaching a steady state of pain response. Some other signal metrics, such as HRV, may have a slow or delayed pain response with an extended transient state before reaching a steady state of pain response. During the pain episode, the pain score generator 233 may generate the pain score using the signal metrics having a quick pain response and short transient state. After an extended period of time following the onset of pain episode, the pain score generator 233 may generate the pain score further using the signal metrics having a delayed pain response to allow the signal metrics to reach steady response state.

In an example, pain score generator 233 may determine the multi-sensor indicated pain score further using the patient demographic information, such as patient age, gender, race, weight, patient medical history, co-morbid disease conditions, or progression of disease conditions among others. For example, males may have higher sympathetic nerve system activity and stronger response to higher levels of pain than females. The pain score generator 233 may tune the threshold values based on the gender of the patient, such as by programming a higher pain threshold for the composite signal metric for male patients than for female patients. Additionally or alternatively, the weight generator 232 may determine or adjust the respective weight factors further based on patient demographic information. In an example, the weight factors for the signal metrics may be tuned to a lower value than the weight factors for the same signal metric in a female patient. In some examples, the pain score generator 233 may also adjust the pain score based on the patient's sleep/awake state or time of the day when a pain episode occurs. For example, the pain score may be lowered when the patient is asleep or during a programmed night time, while the pain score can be increased when the patient is awake or during the programmed daytime. Some disease conditions such as heart failure are associated with autonomic dysfunction. Measures of elevated sympathetic tone in these patients may not be as reliable. In such patients with heart failure as a co-morbid condition, signal metrics reflective of elevated sympathetic tone, such as heart sound, heart rate, or heart rate variability may be weighted down.

The user interface 234 may include an output unit, which may include a display, to present to a system user such as a clinician the multi-sensor indicated pain score. The output unit may also display information including the physiological and functional signals, trends of the signal metric, or any intermediary results for pain score calculation such as the correlations between the pain scales P and the signal metrics, or signal metric-specific pain score, among others. The information may be presented in a table, a chart, a diagram, or any other types of textual, tabular, or graphical presentation formats, for displaying to a system user. The presentation of the output information may include audio or other human-perceptible media format. The user interface 234 may also include input device such as a keyboard, on-screen keyboard, mouse, trackball, touchpad, touch-screen, or other pointing or navigating devices. The input device may enable a system user to program the parameters used for sensing the physiological signals, generating signal metrics, or generating the pain score. In an example, the input device may include a portable electronic device such as a smartphone with a mobile application ("App"). The mobile App may enable a patient to provide pain description or quantified pain scales during the pain episodes, and send the pain description or pain scales to the weight generator 232. In an example, the user interface 234 may enable a system user to confirm, reject, or edit the weight factors determined by the weight generator 232, or to confirm, rejection, or edit the programming of the implantable neuromodulator 210A, such as parameters for electrostimulation.

In an example, the pain score generator 233 may generate the multi-sensor indicated pain score using patient susceptibility of pain. The patient susceptibility may be represented by signal metrics' sensitivity to pain. The pain analyzer 233 may determine the signal metrics' sensitivity to pain by trending the signal metric over time, such as over approximately six months. The signal sensitivity to pain may be represented by a rate of change of the signal metrics over time during a pain episode. The signal sensitivity to pain may be evaluated under a controlled condition such as when the patient posture or activity is at a specified level or during specified time of the day. The weight generator 232 may adjust the respective weight factors further using the signal sensitivity to pain. The pain score generator 233 may generate the multi-sensor indicated pain score using a combination of comparisons between the plurality of the signal metrics and respective threshold values, where the threshold values are proportional to the signal sensitivity to pain.

The programmer circuit 235 may produce parameter values for operating the implantable neuromodulator 210A, including parameters for sensing physiological and functional signals and generating signal metrics, and parameters or electrode configurations for electrostimulation. In an example, the programmer circuit 235 may generate the stimulation parameters or electrode configurations for SCS based on the multi-sensor indicated pain score produced by the pain score generator 233. Through the communication link 120, the programmer circuit 235 may continuously or periodically provide adjusted stimulation parameters or electrode configuration to the implantable neuromodulator 210A. By way of non-limiting example and as illustrated in FIG. 2A, the programmer circuit 235 may be coupled to the user interface 234 to allow a user to confirm, reject, or edit the stimulation parameters, sensing parameters, or other parameters controlling the operation of the implantable neuromodulator 210A. The programmer circuit 235 may also adjust the stimulation parameter or electrode configuration in a commanded mode upon receiving from a system user a command or confirmation of parameter adjustment.

In addition to or in lieu of the pain score which may be used to quantify severity of pain, the pain analyzer 231 may include circuits, or a processor executing instructions, for characterizing various types of pain, such as by differentiating chronic pain from acute pain. In an example, the pain analyzer 231 may trend the signal metric over time to compute an indication of abruptness of change of the signal metrics, such as a rate of change over a specified time period. The pain episode may be characterized as chronic pain if the signal metric changes abruptly (e.g., the rate of change of the signal metric exceeding a threshold), or as acute pain if the signal metric changes gradually (e.g., the rate of change of the signal metric falling below a threshold). The pain therapy may be delivered, withheld, or otherwise modified in accordance with the pain type. For example, incidents such as toe stubbing or bodily injuries may cause abrupt changes in certain signal metrics, but no adjustment of the closed-loop pain therapy is deemed necessary. On the contrary, if the pain analyzer 231 detects chronic pain characterized by gradual signal metric change, then the closed-loop pain therapy may be adjusted accordingly.

Although the pain analyzer 231 is included in the external system 230A, this is meant only by way of example but not limitation. In various embodiments, all or a portion of the pain analyzer 231 may be included in the implantable neuromodulator 210A, or be distributed between the implantable neuromodulator 210A and the external system 230A. In FIG. 2B, a pain management system 200B may comprise an implantable neuromodulator 210B and an external system 230B, which are communicated with each other via the communication link 120. Similar to the implantable neuromodulator 210A, the implantable neuromodulator 210B may include the sensor circuit 211, the signal metrics generator 212, the electrostimulator 213, the controller 214, and the memory 215. Additionally, the implantable neuromodulator 210B may include the pain analyzer 231. The pain analyzer 231 includes the pain score generator 233 that determine a pain score using weight factors stored in the memory 215 and the signal metrics from the signal metrics generator 212 which may also be included in the pain analyzer 231.

The external system 230B may include the user interface 234, the weight generator 232, and the programmer circuit 235. As previously discussed with reference to FIG. 2A, the weight generator 232 may generate weight factors based on correlations between a plurality of pain scales and the measurements of signal metrics corresponding to the pain scales. The programmer circuit 235, which may be coupled to the weight generator 232, may program the implantable neuromodulator 210B via the communication link 120, including transmitting the weight factors generated by the weight generator 232 to the implantable neuromodulator 210B, and store the weight factors in the memory 215. In an example, the weight factors received from the external system 230B may be compared to previously stored weight factors in the memory 215. The controller 214 may update the weight factors stored in the memory 215 if the received weight factors are different than the stored weights. The pain analyzer 231 may use the updated weight factors to generate a multi-sensor indicated pain score. In an example, update of the stored weight factors may be performed continuously, periodically, or in a commanded mode upon receiving a command from a user.

In some examples, the multi-sensor indicated pain score may be used by a therapy unit (such as an electrostimulator) separated from the pain management systems 200A or 200B. In various examples, the pain management systems 200A or 200B may be configured as a monitoring system for pain characterization and quantification without delivering closed-loop electrostimulation or other modalities of pain therapy. The pain characterization and quantification may be provided to a system user such as the patient or a clinician, or to a process such as automatic generation of recommendations or an alert to the system user regarding pain medication (e.g., medication dosage and time for taking a dose), electrostimulation therapy, or other pain management regimes. The therapy recommendations or alert may be based on the multi-sensor indicated pain score, and may be presented to the patient or the clinician in various settings including in-office assessments (e.g. spinal cord stimulation programming optimization), in-hospital monitoring (e.g. opioid dosing during surgery), or ambulatory monitoring (e.g. pharmaceutical dosing recommendations).

In an example, in response to the multi-sensor indicated pain score exceeding a threshold which indicates elevated pain symptom, an alert may be generated and presented at the user interface 234, such as via a mobile App, to remind the patient to take pain medication. In another example, therapy recommendations or alerts may be based on information about wearing-off effect of pain medication, which may be stored in the memory 215 or received from the user interface 234. When the drug effect has worn off, an alert may be generated to remind the patient to take another dose or to request a clinician review of the pain prescription. In yet another example, before a pain therapy such as neurostimulation therapy is adjusted (such as based on the multi-sensor indicated pain score) and delivered to the patient, an alert may be generated to forewarn the patient or the clinician of any impending adverse events. This may be useful as some pain medication may have fatal or debilitating side effects. In some examples, the pain management systems 200A or 200B may identify effect of pain medication addition such as based on functional and physiological signals. An alert may be generated to warn the patient about effects of medication addiction and thus allow medical intervention.

In some examples, if the programmer circuit 235 produces neurostimulation parameter values for closed-loop pain therapy but the neurostimulation parameter is determined based on signal metrics that change in a undesirable or inappropriate direction, then a red-flag alert may be generated and presented to the system user such as via the user interface 234 to warn of such an effect. For example, if an inappropriate or generally undesired change in a signal metric (e.g., decrease in HRV) is associated with less pain and thus used to drive the closed-loop neurostimulation, a red-flag alert may be issued to warn the user that the signal metric (e.g., HRV) for use in programming the closed-loop pain therapy is outside of a generally recognized desirable range.

Figure 3:
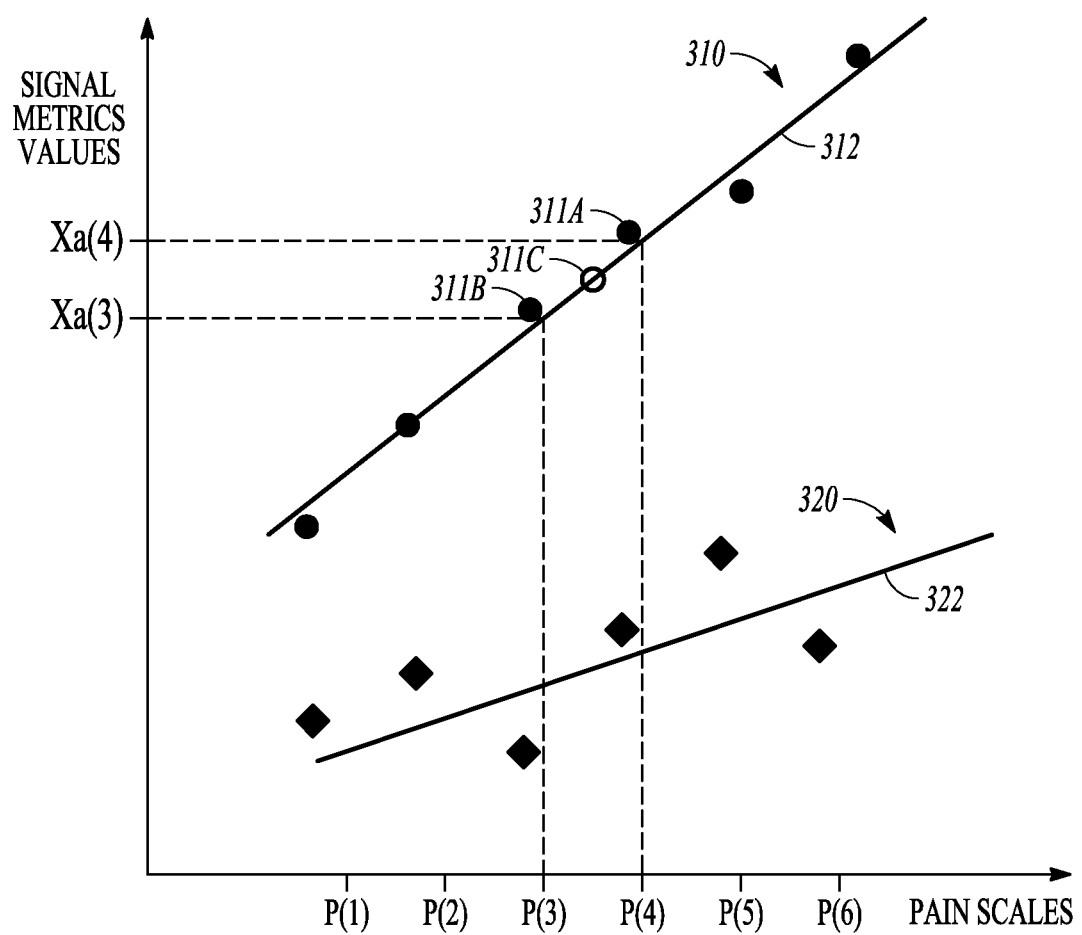
FIG. 3 illustrates, by way of example and not limitation, correlations between pain scales P and the corresponding measurements of two signal metrics.

FIG. 3 illustrates, by way of example and not limitation, correlations between pain scales P and the corresponding measurements of two signal metrics Xa and Xb. The signal metrics Xa and Xb may be generated by the signal metrics generator 212 from different physiological or functional signals. In an example, Xa is a heart rate variability (HRV) and Xb is an expression level of BNP or NT-proBNP. The signal metrics Xa and Xb may also be different signal metrics generated from the same physiological or functional signals. In an example, Xa is a HR trend and Xb is a HRV trend, both of which are generated from a ECG signal.

As illustrated in FIG. 3, Xa measurements 310 and Xb measurements 320 may correspond to various levels of pain scales such as P(1) through P(6), as depicted in the horizontal axis. The pain scales may be provided by the patient such as via the user interface 234 during one or more spontaneous pain episodes in the patient medical history, or during one or more induced pain episodes such as in a pain assessment session administered by a clinician.

The Xa measurements 310 may be fit to a linear regression line 312. Similarly, Xb measurements 320 may be fit to a linear regression line 322. Other curve fitting, such as exponential, parabolic, polynomial, or piecewise linear may alternatively be used. The slope of the linear regression line may indicate the signal metric's sensitivity to a variation in pain scale. For example, a steep slope may indicate a pronounced change in the signal metric, thus a higher sensitivity to the change in pain scale, than a flat slope. The spreadness of the signal metric measurements with respect to the regression line may graphically indicate a correlation between the signal metric and the pain scales. As illustrated in FIG. 3, Xa measurements 310 are more tightly distributed about the regression line 312 than the Xb measurements 320 distributed about the regression line 322. Xa thus demonstrates a closer correlation with the pain scales than Xb. The weight generator 232 may assign a larger weight to signal metric Xa than to signal metric Xb at least based on such differences in correlations. In some examples, the correlation may be normalized by variance of the signal metric measurements and the variance of the pain scales, resulting in a correlation coefficient taking a value between 0 and 1. The weight generator 232 may determine the weight factors based on the correlation coefficient, or the slope of the regression line.

In some examples, the pain scales, such as provided by the patient during one or more pain episodes, may be interpolated or extrapolated based on the given pain scales P. The measurements of the signal metrics may also be interpolated or extracted among the measured values corresponding to the pain levels P. The correlations between the interpolated or extrapolated pain scales and the interpolated or extrapolated signal metrics measurements corresponding to the interpolated or extrapolated pain scales may then be determined. The linear regression between the signal metrics Xa or Xb to the pain scales, such as represented by the regression lines 312 and 322, may be used to determine a signal metric-specific pain score. For example, a measurement of Xa at 311C with a value between Xa(3) and Xa(4) may have a corresponding pain score between P(3) and P(4), based on the regression line 312. Additionally or alternatively the pain score corresponding to the measurement 311C may be determined based on interpolation or extrapolation from the measurements such as 311A and 322B. The pain score generator 233 may use the signal metric-specific pain score to generate the multi-sensor indicated pain score.

Figure 4A:
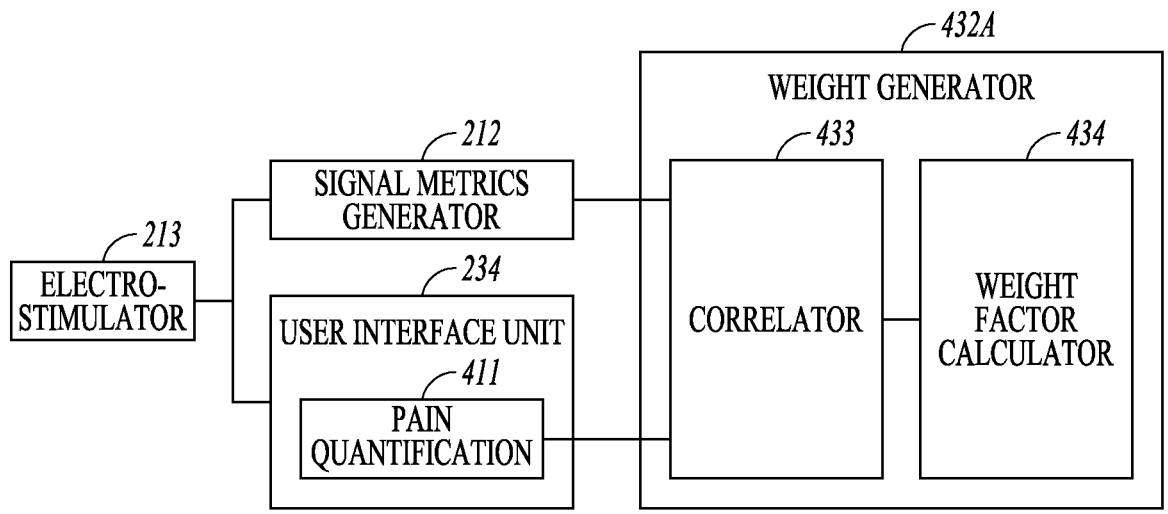
FIGS. 4A-D illustrate, by way of example and not limitation, portions of a pain management system for generating weight factors for the respective signal metrics.

FIGS. 4A-D illustrate, by way of example and not limitation, portions of a pain management system for generating weight factors for the respective signal metrics. Weight generators 432A-D may each be an embodiment of the weight generator 232. In FIG. 4A, a weight generator 432A may include a correlator 433 and a weight factor calculator 434. The correlator 433 may receive from the user interface unit 234 pain quantification 411 such as a plurality of pain scales, such as provided by the patient, when the electrostimulator 213 delivers programmed electrostimulation energy to induce one or more pain episodes. In an example, the electrostimulator 213 may be programmed, such as by a clinician during a patient follow-up, to execute a pain assessment protocol that includes different levels of stimulation energy for pain therapy. The different stimulation energy levels may be achieved by adjusting the pulse intensity, duration, frequency, on/off period, or electrode selection and stimulation vector configuration, among other therapy parameters. In an example, the pain assessment protocol may include a low stimulation energy level such as by temporarily withholding delivery of electrostimulation, a high stimulation energy level such as by delivering the maximal tolerable and safe stimulation as prescribed by the clinician, and optionally one or more intermediate stimulation energy levels between the minimal and maximal energy levels. In some examples, the pain assessment protocol may include non-pain related tasks such as stress, leg lift, grip test that result in changes in some physiological or functional signals. Results from such tests may be used to discriminate between painful states and other states such as activity and stress.

Corresponding to the various stimulation energy levels, a patient with chronic pain may experience various degrees of pain symptoms. For example, the patient may sense severe pain when the electrostimulation is withheld, and no pain or slight pain when the maximal tolerable stimulation energy is delivered. The pain assessment protocol may include respective durations for each stimulation energy level, such as to allow patient adaptation to changes of stimulation energy from one level to another, and to allow stabilization of patient physiological responses and pain sensation. The stimulation energy levels may be arranged in a ramp-up, a ramp-down, an intermittent, or a random order, among others.

The pain quantification 411, as provided by the patient during the execution of the pain assessment protocol, may include numerical values or categorical values. The numerical values may be discrete or continuous within specified bounds such as between 0 and 10. The categorical values may include "low", "medium", or "high". In an example, the pain quantification 414 may include patient qualitative pain description, such as a pain drawing or a patient questionnaire that may include information of anatomical location and distribution of the pain, severity or intensity of pain at various pain locations, or temporal pattern such as persistence of the pain at various pain locations. For example, the pain drawing can include illustrative images of human body (such as including one or both of anterior/ventral or posterior/dorsal images) with the pain markings provided by the subject. The pain markings identify the anatomical locations where pain radiates or expands. The pain markings may be created to indicate pain the subject presently senses, or suffers within a specified period of time, such as in past seven days prior to the time of marking. The pain markings can additionally include the different markings to distinguish various pain sensations such as aching, numbness, burning, stabbing, or needle pain, among others, and/or different markings to distinguish intensity of the pain sensations at different marked pain locations. The patient subjective pain description may then be transformed into quantitative pain scales.

The signal metrics generator 212 may produce measurements of a plurality of signal metrics when the electrostimulator 213 induces one or more pain episodes. The signal metrics may be generated from physiological or functional signals that are sensed during the pain assessment protocol. The correlator 433 may determine a correlation between the pain quantification 411 such as the pain scales based on patient input and the signal metrics measurements corresponding to various pain scales. In an example, measurements of a signal metric and the pain scales may be displayed in a user interface such as illustrated in FIG. 3. The correlator 433 may perform regression analysis and determine a regression line or curve that fits the data. The slope or trend of the fitted line or curve may indicate the sensitivity of the signal metric to pain. The weight factor calculator 434 may generate weight factors based on the correlations. In an example, the weight factors may be proportional to the correlations.

Figure 4B:
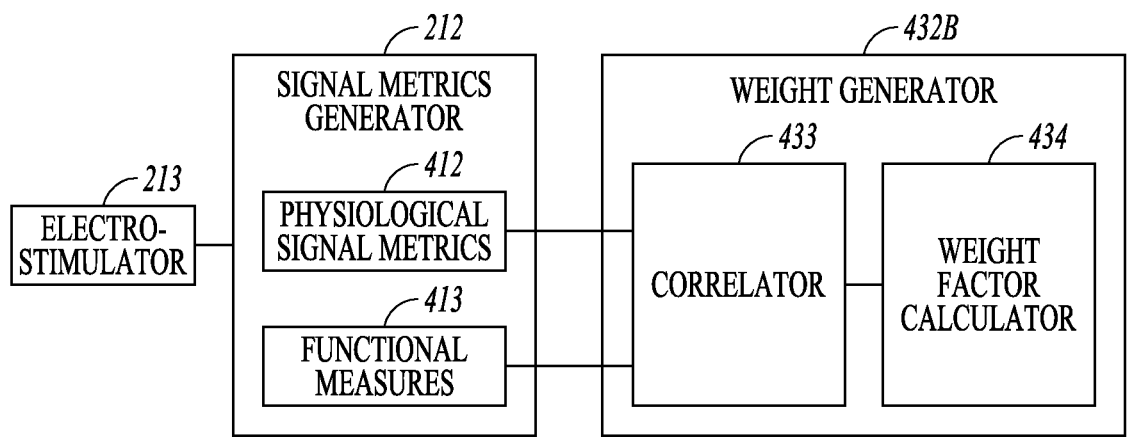

FIG. 4B illustrates a weight generator 432B that may include the correlator 433 and the weight factor calculator 434. The correlator 433 may be coupled to the signal metrics generator 212, and compute correlations between physiological signal metrics 412 and functional measures 413. The physiological metrics 412 may include cardiac, pulmonary, neural, or biochemical signals that may demonstrate signal characteristic changes in response to onset, intensity, severity, duration, or different patterns of pain. The functional measures 413 may include a posture, a gait, a balance indicator, a locomotion pattern, or a physical activity. The physiological signals metrics 412 and the functional measures 413 may be simultaneously measured during induced pain episodes such as when the electrostimulator 213 executes the pain assessment protocol, as previously discussed with reference to FIG. 4A. The functional measures may be related to, and have a pre-determined correlation with, the pain scales (P). For example, a patient may demonstrate distinct gaits or locomotion patterns under different pain severity, persistence, patterns, or anatomical areas. A correspondence between such functional measures and the pain suffered may be specified and stored in the device memory 215. The correlation between the physiological signal metrics 412 and the functional measures 413 may thus indirectly indicate correlations between the physiological signal metrics 412 and the pain scales. Compared to the functional measures, the correspondence between the physiological signal metrics and the pain symptom may not be feasibly determined in some patients, or such correlation may be more subject to inter- or intra-patient variation. Additionally, acquiring subjective description or patient-specified pain scale may not be feasible in some patients such as those with speech or mental disorders. The correlation between physiological signal metrics 412 and functional measures 413 may be more feasible to determine the correlation and the weight factors for the physiological signal metrics in such patients.

In some examples, the functional measures 413 may be used in combination with the patient pain quantification 411 for determination of the correlation to the signal metrics such as a physiological signal metric. In an example, the functional measures 413, such as activity, posture, or gait, may be used to further adjust the weight factors determined based on the correlations between the signal metrics and pain quantifications 414. For example, between physiological signal metrics Xa and Xb that correlate almost equally well with the pain quantification, if the functional measures 413 correlates with Xa more closely than with Xb, then a greater weight may be assigned to Xa.

Figure 4C:
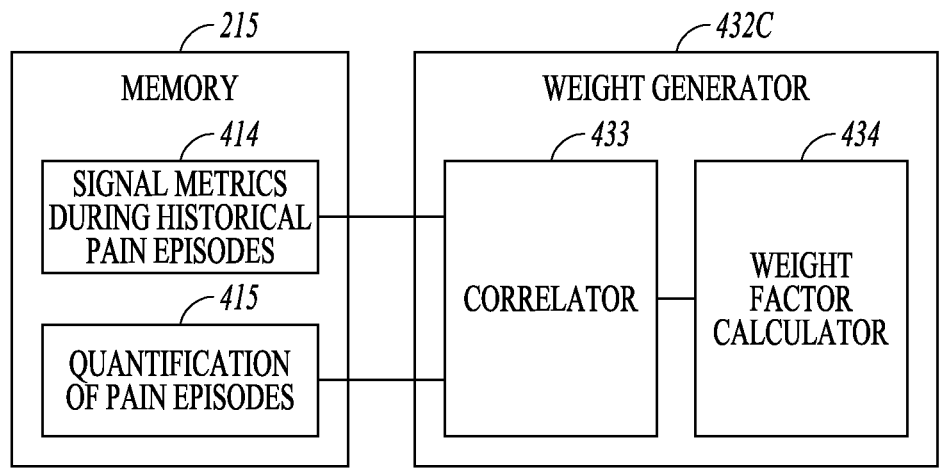

FIG. 4C illustrates a weight generator 432C that may include the correlator 433 and the weight factor calculator 434. The correlator 433 may be coupled to the memory 215 and generate the correlations between the signal metrics 414 sensed during one or more historical pain episodes and the quantification of pain episodes 415. Instead of inducing pain episodes by programming the electrostimulator to execute a pain assessment protocol (as discussed previously with reference to FIG. 4A), the signal metrics measurements and the pain quantification are pertaining to, and acquired during, patient historical spontaneous pain episodes such as occurred in an ambulatory setting. The historical pain episodes may occur at different time in an extended period of time, such as approximately within past 1-6 months or approximately one year. Upon an onset of a pain session, the sensors may record physiological or functional signals, automatically or activated at least partially by the patient.

The patient may provide sensed pain scales or pain description at different stages of the pain session. The user-provided pain quantification and the signal metrics measurements may be stored in the memory 215. The correlations may be used to determine the weight factors for the signal metrics, as previously discussed with reference to FIG. 4A.

In various examples, the weight factor calculator 434 in FIGS. 4A-C may determine a variable weight factor for a signal metric. An example of the variable weight factor may include a pain scale-dependent weight factor, where the weight factor may change over the range of pain scales corresponding to various severities of pain symptoms. For example, some biomarkers may become more or less relevant in various ranges of pain perception. Accordingly, for a particular biomarker, a variable weight factor may include a higher weight at a first pain scale and a lower weight at a different second pain scale.

Figure 4D:
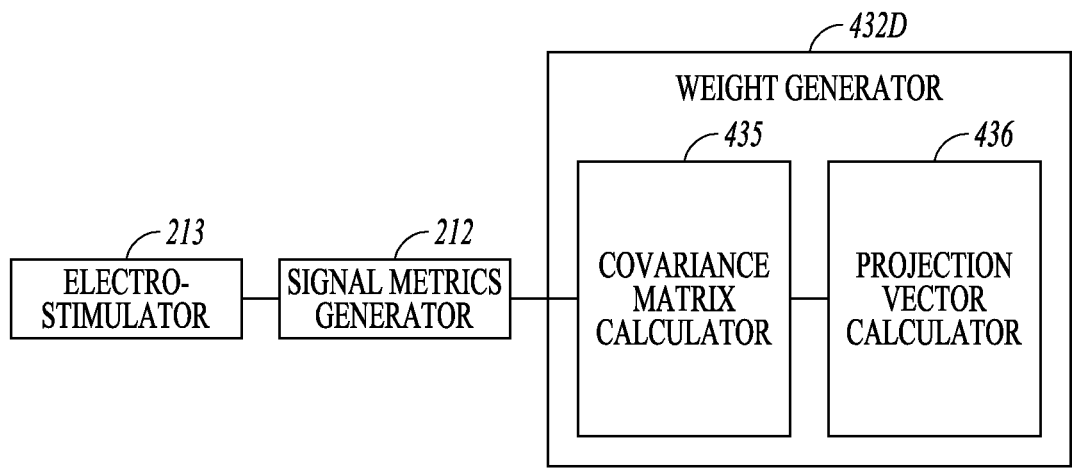

FIG. 4D illustrates a weight generator 432D that may include a covariance matrix calculator 435 and a projection vector calculator 436. The covariance matrix calculator 435 may receive from the signal metrics generator 212 signal metrics that are measured when the electrostimulator 213 delivers or withholds the electrostimulation therapy for pain treatment. In an example, the covariance matrix calculator 435 may compute a first covariance matrix ($\Sigma_A$) based on a plurality of signal metrics generated from the functional or physiological signals sensed during a historical or induced pain episode with a first pain scale, and a second covariance matrix ($\Sigma_B$) based on the plurality of signal metrics generated from the functional or physiological signals sensed during a historical or induced pain episode with a second pain scale. In an example, the first pain scale corresponds to no delivery of electrostimulation (such as by temporarily withholding the electrostimulation) such that a high degree of pain is perceived by the patient, and the second pain scale corresponds to a delivery of high, safe and tolerable electrostimulation energy that results in no or minimal pain symptom. The covariance matrix calculator 435 may additionally perform a matrix transformation on the covariance matrices $\Sigma_A$ and $\Sigma_B$, such as a principal component analysis (PCA) that may simplify the covariance matrices by limiting the covariance among different signal metrics to more informative dimensions in the multi-dimensional feature space.

The projection vector calculator 436 may determine a projection vector in indicating a projection direction in a multi-dimensional feature space for pain quantification. In an example, the projection may be determined using a Fischer's linear discriminant. The projection vector calculator 436 may compute a first average feature vector ($\mu_A$) of the signal metrics corresponding to the first pain scale, and a second average feature vector ($\mu_B$) of the signal metrics corresponding to the second pain scale. The projection vector that indicates a direction in the multi-dimensional feature space that separates the signal metrics measurements during the first pain scale (such as maximal pain when electrostimulation is withheld) from the signal metrics measurements during the second pain scale (such as no or minimal pain when high, stimulation is delivered) may be determined according to Equation (1):

$$p = (\Sigma_A + \Sigma_B)^{-1}(\mu_A - \mu_B) \quad (1)$$

The pain score generator 233 may generate the pain score by projecting the sensed plurality of the signal metrics onto the projection vector using vector multiplication $p^T X$, where T denotes vector transpose, and X denotes measurements from multiple signal metrics. Because the entries of the projection vector p are weight factors for the respective signal metrics, the projection operation effectuates a linear combination of the signal metrics each weighted by respective weight factors in the projection vector p.

Figure 5:
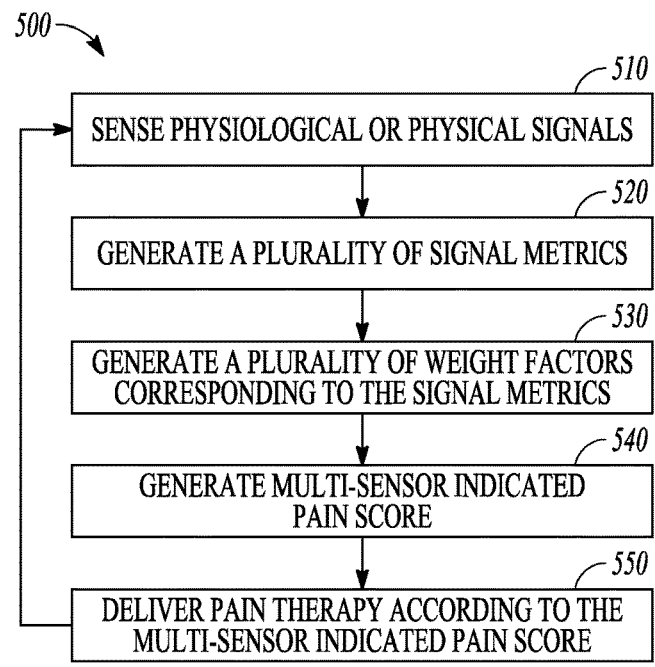
FIG. 5 illustrates, by way of example and not limitation, a method for managing pain in a patient.

FIG. 5 illustrates, by way of example and not limitation, a method 500 for managing pain in a patient. The method 500 may be implemented in a medical system, such as the pain management system 200A or 200B. In an example, at least a portion of the method 500 may be executed by a neuromodulator device (IND) such as the implantable neuromodulator 210A or 210B. In an example, at least a portion of the method 500 may be executed by an external programmer or remote server-based patient management system, such as the external system 230A or 230B that are communicatively coupled to the IND. The method 500 may be used to provide neuromodulation therapy, such as spinal cord stimulation, to treat chronic pain or other disorders.

The method 500 begins at step 510, where two or more physiological or functional signals may be sensed such as via electrodes or ambulatory sensors associated with the patient. Examples of the physiological signals may include cardiac, pulmonary, or neural signals, such as, by way of example of limitation, electrocardiograph (ECG) or intracardiac electrogram, heart rate signal, heart rate variability signal, cardiovascular pressure signal, or heart sounds signal, respiratory signal, a thoracic impedance signal, or a respiratory sounds signal, or neural activity signal. The physiological signals may also include blood chemistry measurements or biomarkers that are indicative of onset, intensity, severity, duration, or different patterns of pain. Examples of functional signals may include patient posture, gait, balance, physical activity signals, or signals indicating sleep or awake state, among others. Such functional signals may responsively co-variate with a pain episode. In an example, the functional signals may be sensed using accelerometer sensors.

At 520, a plurality of signal metrics may be generated from the sensed physiological or functional signals. The signal metrics may include statistical parameters, morphological parameters, or temporal parameters. Examples of the signal metrics for assessing pain may include heart rate, heart rate variability, intensity of one or more heart sounds components such as S1, S2, S3 or S4 heart sounds or relative intensity such as a ratio between two heart sound components, a respiratory rate, a tidal volume, or a rapid-shallow breathing index (RSBI) computed as a ratio of a respiratory rate measurement to a tidal volume measurement, physical activity intensity, or a time duration when the activity intensity is within a specified range or above a specified threshold, or gait or locomotion pattern, etc.

At 530, a plurality of weight factors may be generated corresponding to the signal metrics. The weight factors indicate the corresponding signal metrics' reliability in representing an intensity of the pain. To take into account the differences in reliability across different signal metrics, the weight factors may be determined individually for the signal metric to emphasize or de-emphasize one signal metric's contribution to pain quantification over another signal metric. A sensor metric that is more reliable, or more sensitive or specific to the pain, may be assigned a larger weight than another sensor metric that is less reliable, or less sensitive or specific to the pain. In an example, the weight factors may be determined based on correlations between a plurality of quantified pain scales and measurements of the plurality of signal metrics corresponding to the plurality of quantified pain scales. The correlations provide a quantitative measure of reliability of the signal metrics in characterizing the pain.

In an example, the weight factors may be proportional to the correlations, such that a signal metric having a higher correlation with the pain scales may be assigned a higher weight factor than a signal metric having a lower correlation with the pain scales. Examples of the method for generating respective weight factors for the signal metrics are discussed below, such as with reference to FIG. 6.

At 540, a multi-sensor indicated pain score may be generated using the measurements of the signal metrics and the weight factors. The multi-sensor indicated pain score may be represented as a numerical or categorical value that quantifies overall pain quality in the subject. In an example, a composite signal metric may be generated using a linear or nonlinear combination of the signal metrics weighted by the respective weight factors. The composite signal metric may be categorized as one of a number of degrees of pain by comparing the composite signal metric to one or more threshold values or range values, and a corresponding pain score (such as numerical values from 0 to 10) may be assigned based on the comparison. In another example, each signal metric may be compared to a respectively specified threshold or range values and a corresponding signal metric-specific pain score may be determined.

A multi-sensor indicated pain score may be generated using a linear or nonlinear fusion of the signal metric-specific pain scores each weighted by their respective weight factors. Examples of the fusion algorithm may include decision trees, voting, weighted averages, or neural networks, among others. In some examples, the multi-sensor indicated pain score may be computed using a subset of the signal metrics selected based on their temporal profile of pain response. Signal metrics with quick pain response (or a shorter transient state of response) may be selected to compute the multi-sensor indicated pain score during a pain episode. Signal metrics with slow or delayed pain response (or a longer transient state of response before reaching a steady state) may be used to compute the multi-sensor indicated pain score after an extended period following the onset of pain such as to allow the signal metrics to reach steady state of response. In some examples, patient demographic information such as patient age or gender may be used in computing the multi-sensor indicated pain score. A higher pain threshold for the composite signal metric may be selected for male patients than for female patients. Additionally or alternatively, the respective weight factors may be determined based on patient demographic information. The weight factors for the signal metrics may be tuned to a lower value than the weight factors for the same signal metric in a female patient.

At 550, a pain therapy may be delivered to the patient according to the multi-sensor indicated pain score. Examples of the pain therapy may include spinal cord stimulation (SCS) via electrodes electrically coupled to the electrostimulator. The SCS may be in a form of stimulation pulses that are characterized by pulse amplitude, pulse width, stimulation frequency, duration, on-off cycle, waveform, among other stimulation parameters. In an example, the pain therapy such as SCS may be determined based on the multi-sensor indicated pain score. In an example, the pain therapy may be delivered in a closed-loop fashion, which may include adaptive adjustment of one or more stimulation parameters or stimulation electrode configuration based on the multi-sensor indicated pain score. The parameter adjustment or stimulation electrode configuration may be executed continuously, periodically at specified time, duration, or frequency, or in a commanded mode upon receiving from a system user a command or confirmation of parameter adjustment. Efficacy of the delivered pain therapy may be evaluated and the weight factors may be updated based on the pain-relieving effect. The method 500 may proceed at 510 to sense physiological or functional signals such as in response to the therapy delivered at 550. Examples of closed-loop pain therapy are discussed below such as with reference to FIG. 7.

Figure 6:
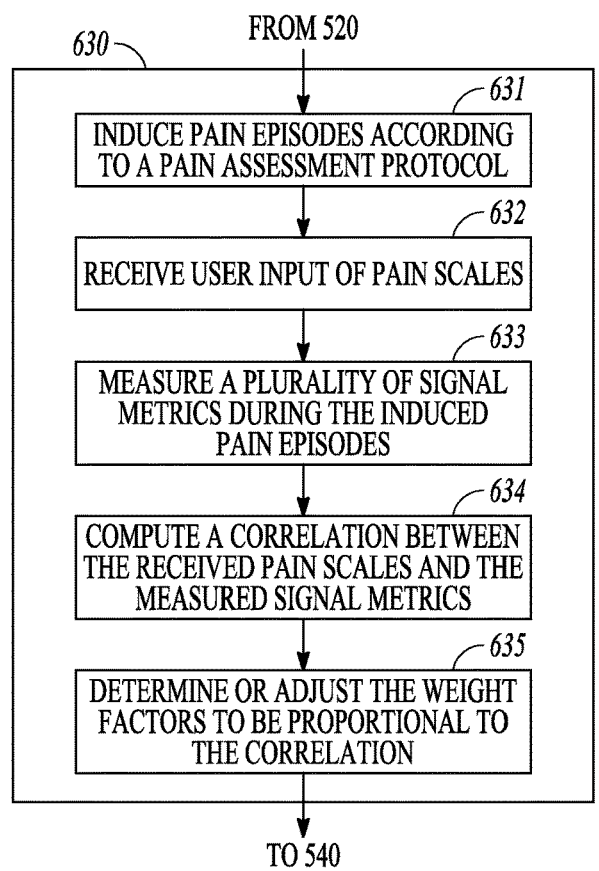
FIG. 6 illustrates, by way of example of not limitation, a method for generating the weight factors for the signal metrics.

FIG. 6 illustrates, by way of example of not limitation, a method 630 of generating the weight factors for the signal metrics. The method 630, which may be an embodiment of the weight factor generation at 530 of the method 500, may be implemented in and executed by the system portion as illustrated in FIG. 4A.

The method 630 begins at 631 with an induction of pain episodes using programmed electrostimulation. In an example, induction of pain episodes may include a pain assessment protocol that includes trains of electrostimulation at different levels of stimulation energy for pain therapy, such as during a patient follow-up visit in a clinic. The different stimulation energy may be achieved by adjusting the pulse intensity, duration, frequency, on/off period, or electrode selection and stimulation vector configuration, among other therapy parameters. In an example, the pain assessment protocol may include a low stimulation energy level such as by temporarily withholding electrostimulation, a high stimulation energy level such as by delivering the maximal tolerable and safe level of stimulation as prescribed by the clinician, and optionally one or more intermediate stimulation energy states between the minimal and maximal energy for pain treatment. A patient with chronic pain may experience various degrees of pain symptoms corresponding to the stimulation energy levels. The pain assessment protocol may include respective durations for each stimulation energy level, such as to allow patient adaptation to changes of stimulation energy from one level to another, and to allow stabilization of patient physiological responses and pain sensation. The stimulation energy levels may be arranged in a ramp-up, a ramp-down, an intermittent, or a random order.

At 632, a user input of pain scales perceived during the induced pain episodes may be provided by the patient. The pain scales may include numerical values or categorical values. In some examples, the user input may include patient qualitative pain description such as a pain drawing or a patient questionnaire. The qualitative pain description may be transformed to pain scales, such as a discrete or continuous numeric value between 0 and 10.

At 633, a plurality of signal metrics may be measured during the induced pain episodes. The signal metrics may be generated from physiological or functional signals that are sensed during the induced pain episodes when electrostimulation is delivered according to the pain assessment protocol. At 634, correlations Corr(P, X) between the pain scales (P) and the signal metrics measurements (X) corresponding to various pain scales may be computed. The signal metric measurements and the pain scales may be graphically presented to a system user such as to be displayed in the user interface 234. A regression analysis may be performed to determine a regression line or curve that fits the pain scales and the signal metric measurements during the induced pain episodes, such as the graph shown in FIG. 3. The correlation Corr(P, X) may be graphically represented by the spreadness of the signal metric measurements with respect to the regression line. The slope or trend of the fitted line or curve may indicate the sensitivity of the signal metric to the pain. Based on the regression line or curve, a signal metric measurement may be mapped to the corresponding signal metric-specific pain score, such as by using interpolation or extrapolation of the measured signal metrics between or beyond the user input of the pain scales. The signal metric-specific pain scores may each be weighted by their respective weight factors to generate the multi-sensor indicated pain score.

In some examples, by using the system portion as illustrated in FIG. 4B, patient historical spontaneous pain episodes such as occurred in an ambulatory setting may be used in addition to or in lieu of the induced pain episodes at 631. The historical pain episodes may occur at different time in an extended period of time, such as approximately within past 1-6 months or approximately one year. Upon an onset of a pain session, at 632 the patient may provide sensed pain scales or pain description at different stages of the pain session, and at 633 the signal metrics may be generated from the physiological or functional automatically or activated by the patient. The user-provided pain quantification and the signal metrics measurements may be stored in a memory, and retrieved for computing the correlations between the received pain scales and the measured signal metrics at 634.

At 635, weight factors for the signal metrics may be determined or adjusted based on the correlations Corr(P, X) computed at 634. The weight factors may be proportional to the correlations Corr(P, X), such that a larger weight may be assigned to a signal metric that is more closely correlated to the pain scales than to another signal metric loosely correlated to the pain scales. The weight factors may be used to generate a multi-sensor indicated pain score at 540.

In some examples, by using the system portion as illustrated in FIG. 4C, correlations between the signal metrics derived from physiological signals and functional measures may be computed. The functional measures may include measurements of posture, a gait, a balance indicator, a locomotion pattern, or a physical activity. The functional measures, which may have pre-determined correlations with the pain scales, may be simultaneously measured during induced or spontaneous pain episodes. The correlation between the physiological signal metrics and the functional measures may indirectly indicate correlations between the physiological signal metrics and the pain scales. The weight factors for the signal metrics may be determined or adjusted based on the correlations between the physiological signal metrics and the functional measures, or optionally in combination with the correlations computed at 634.

In some examples, the weight factor generation method 630 may include generating a projection vector based on covariance matrices of the signal metrics at different pain scales, such as via the system portion as illustrated in FIG. 4D. In an example, a first covariance matrix ($\Sigma_A$) is computed using the signal metrics measured during a pain episode with a first pain scale such as a high degree of pain when no electrostimulation energy is delivered. A second covariance matrix ($\Sigma_B$) is computed using the signal metrics measured during a pain episode with a second pain scale such that a low degree of pain when electrostimulation energy is delivered to alleviate the pain. A Fischer's linear discriminant may be used to compute a projection vector, such as according to Equation (1) presented above. The projection vector indicating a direction in the multi-dimensional feature space that separates the signal metrics measurements during the first pain scale (such as maximal pain when anti-pain stimulation is withheld) from the signal metrics measurements during the second pain scale (such as minimal pain when anti-pain stimulation is delivered). The entries of the projection vector are weight factors for the respective signal metrics. The projection operation is essentially linear combination of the signal metrics each weighted by respective weight factors in the projection vector.

Figure 7:
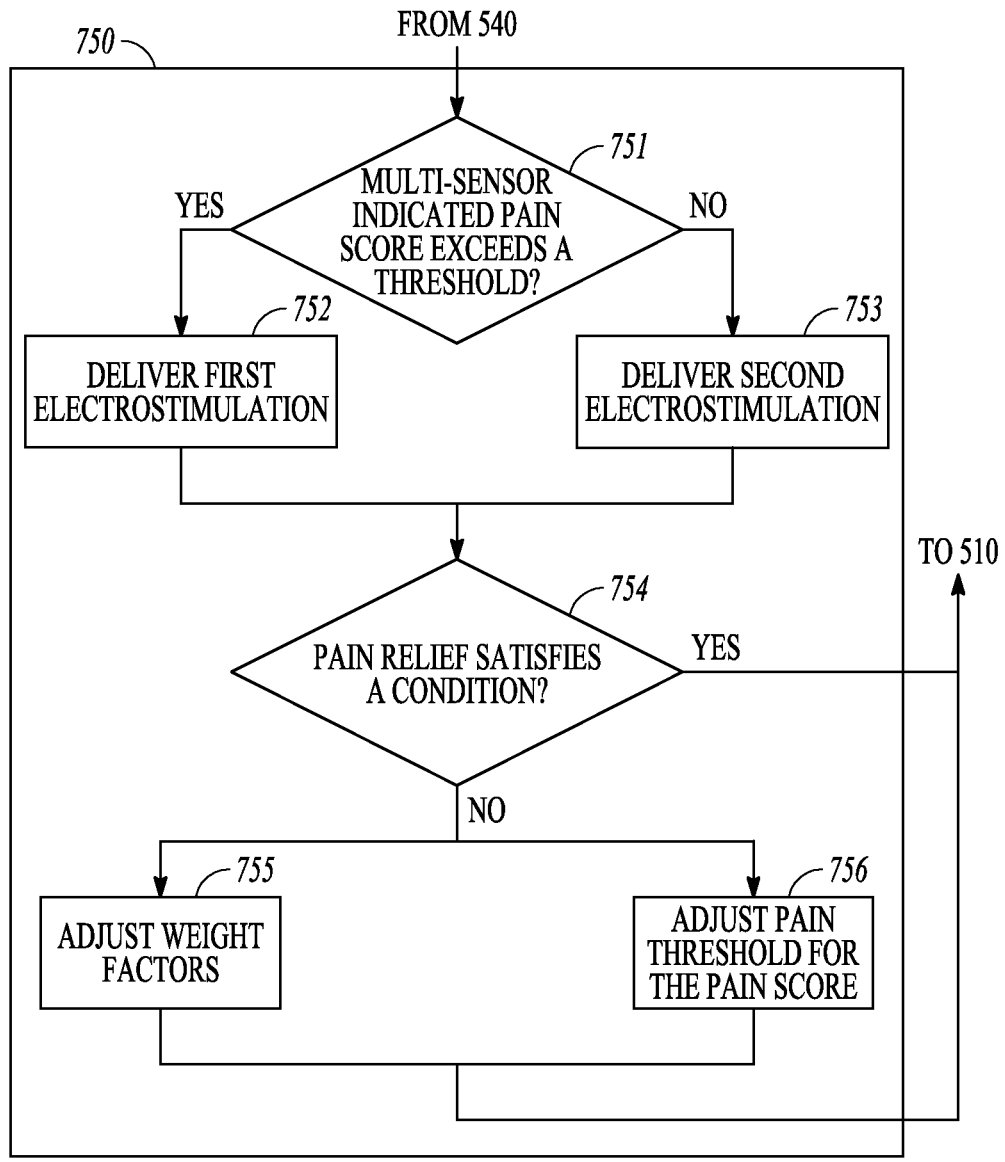
FIG. 7 illustrates, by way of example of not limitation, a method for delivering pain therapy according to the multi-sensor indicated pain score.

FIG. 7 illustrates, by way of example of not limitation, a method 750 for delivering pain therapy according to the multi-sensor indicated pain score. The method 750 may be an embodiment of the therapy delivery at 550 of the method 500. At 751, the multi-sensor indicated pain score computed at 540 may be compared to a pain threshold. If the multi-sensor pain score exceeds the pain threshold (or falls within a specified range indicating an elevated pain), then at 752 a first pain therapy, such as first electrostimulation may be delivered. Conversely, if the multi-sensor pain score falls below a respective threshold value (or falls within a specified range indicating no pain or mild pain), then at 753 a second pain therapy, such as second electrostimulation may be delivered. The first and second electrostimulations may differ in at least one of the stimulation energy, pulse amplitude, pulse width, stimulation frequency, duration, on-off cycle, pulse shape or waveform, temporal pattern of the stimulation, among other stimulation parameters. In an example, the first electrostimulation may have higher energy than the second electrostimulation, such as to provide stronger effect of pain relief. Examples of increased electrostimulation energy may include a higher pulse intensity, a higher frequency, a longer stimulation duration or "on" cycle, among others.

At 754, the adequacy of pain relief, as provided by the pain therapy at 752 or 753, may be evaluated. The evaluation of pain therapy may include the patient's or a clinician's assessment of the pain relief effect and any side effect associated with the pain therapy. In an example, the evaluation may be provided via the user interface 234. If the pain relief satisfies a specified condition such as achieving or maintaining a desired clinical outcome, then no update of the weight factors or pain threshold is needed, and the method may continue at 510 to sense physiological or functional signals and proceed with pain quantification. If at 754 the pain relief fails to satisfy the specified condition, such as inadequate pain relief or substantial side effects, then the weight factors may be adjusted at 755, and/or the pain threshold for pain score calculation may be adjusted at 756. In some examples, weight factors for various signal metrics may change for a given patient over time. For example, as the patient's health status or weight changes over time, some signal metrics may become more or less sensitive to chronic pain. The weight factors may be modified in accordance with the changes of signal metrics' sensitivities to pain. An alert may be presented to the user who may alter one or more weight factors for the signal metrics. Alternatively, update of the weight factors may be attempted continuously or periodically at specified time, duration, or frequency. The method may continue at 510 to sense physiological or functional signals and proceed with pain quantification using the new weight factors and/or new pain threshold used for pain score calculation.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A system for managing pain in a patient, the system comprising:
    two or more sensors configured to respectively sense two or more signals from the patient, the signals including a physiological or functional signal from the patient;
    a pain analyzer coupled to the two or more sensors, the pain analyzer configured to:
        generate a plurality of signal metrics from the sensed two or more signals and a plurality of weight factors corresponding to the plurality of signal metrics, the weight factors indicating the corresponding signal metrics reliability in representing an intensity of the pain; and
        generate a pain score using a combination of the plurality of signal metrics each weighted by the corresponding weight factor; and
    an output unit configured to output the pain score to a user or a process.

2. The system of claim 1, further comprising:
    an electrostimulator configured to generate electrostimulation energy to treat pain; and
    a controller coupled to the pain analyzer and the electrostimulator, the controller configured to control the electrostimulator to deliver a pain therapy, including controlling the electrostimulation energy generated by the electrostimulator according to the pain score.

3. The system of claim 1, wherein the electrostimulator is configured to deliver spinal cord stimulation (SCS) via one or more electrodes positioned at a target site on or near a spinal cord of the patient.

4. The system of claim 1, wherein:
    the physiological signal is selected from the group of signals consisting of:
    a heart rate signal;
    a heart rate variability signal;
    a heart sounds signal;
    a thoracic impedance signal;
    a respiration signal; and
    one or more biochemical signals; and
    the functional signal is selected from the group of signals consisting of:
    a posture;
    a gait;
    a balance indicator; and
    a physical activity.

5. The system of claim 1, wherein the pain analyzer includes a weight generator configured to:
    compute correlations between a plurality of quantified pain scales and measurements of the plurality of signal metrics corresponding to the plurality of quantified pain scales; and
    determine or adjust the weight factors to be proportional to the correlations.

6. The system of claim 5, including a memory configured to store the plurality of quantified pain scales including quantification of one or more historical pain episodes; and
    wherein the weight generator is configured to determine the correlations between (1) the quantification of the one or more historical pain episodes and (2) the plurality of signal metrics measured during the one or more historical pain episodes.

7. The system of claim 5, including a user interface configured to receive user input of the plurality of quantified pain scales when the electrostimulator delivers programmed electrostimulation energy to induce one or more pain episodes; and
    wherein the weight generator is configured to determine the correlations between (1) the user input of the plurality of quantified pain scales and (2) the plurality of signal metrics measured during the one or more induced pain episodes.

8. The system of claim 5, wherein the pain analyzer is configured to determine or adjust the respective weight factors further based on patient demographic information.

9. The system of claim 5, wherein the pain analyzer is configured to:
    determine, for the plurality of signal metrics, respective signal sensitivity to pain; and
    determine or adjust the respective weight factors further using the signal sensitivity to pain,
    wherein the signal sensitivity to pain includes a rate of change of the signal metrics over time during a pain episode.

10. The system of claim 9, wherein the pain analyzer is configured to generate the pain score using a combination of comparisons between the plurality of the signal metrics and respective threshold values, wherein the threshold values are proportional to the signal sensitivity to pain.

11. The system of claim 5, wherein the pain analyzer is configured to:
    generate a projection vector using (1) a first covariance matrix of first plurality of signal metrics generated from the physiological or functional signals sensed during a historical or induced pain episode with a first pain scale and (2) a second covariance matrix of second plurality of the signal metric generated from the physiological or functional signals sensed during a historical or induced pain episode with a second pain scale; and
    generate the pain score including a projection of the sensed plurality of the signal metrics along a direction of the projection vector.

12. The system of claim 1, wherein the pain analyzer is configured to differentiate chronic pain from acute pain based on an abruptness of signal metric change over a specified time period.

13. The system of claim 1, including an implantable neuromodulator device (IND) and an external system communicatively coupled to the IND, wherein:
the IND includes at least a portion of the pain analyzer, the electrostimulator, and sensor circuits coupled to the two or more sensors; and
the external system includes the weight generator and a programmer configured to program the electrostimulator including programming the pain therapy according to the pain score.

14. A method for managing pain in a patient using an implantable neuromodulator device (IND), the method comprising:
sensing two or more signals from the patient via two or more sensors, the signals including physiological or functional signals;
generating a plurality of signal metrics from the sensed two or more signals;
generating a plurality of weight factors corresponding to the plurality of signal metrics, the weight factors indicating the corresponding signal metrics' reliability in representing an intensity of the pain;
generating a pain score using a combination of the plurality of signal metrics each weighted by the corresponding weight factor; and
delivering a pain therapy via the IND, the pain therapy including electrostimulation energy determined according to the pain score.

15. The method of claim 14, wherein the pain therapy includes spinal cord stimulation (SCS) of a target site on or near a spinal cord of the patient.

16. The method of claim 14, wherein the determination of the electrostimulation energy includes increasing the electrostimulation energy in response to the pain score exceeding a threshold, or decreasing the electrostimulation energy in response to the pain score falling below a threshold.

17. The method of claim 14, wherein generating a plurality of weight factors includes:
computing correlations between a plurality of quantified pain scales and measurements of the plurality of signal metrics corresponding to the plurality of quantified pain scales; and
determining or adjusting the weight factors to be proportional to the correlations.

18. The method system of claim 14, further comprising generating a projection vector using (1) a first covariance matrix of first plurality of signal metrics generated from the physiological or functional signals sensed during a historical or induced pain episode with a first pain scale and (2) a second covariance matrix of second plurality of the signal metric generated from the physiological or functional signals sensed during a historical or induced pain episode with a second pain scale;
wherein generating the pain score includes computing a projection of the sensed plurality of the signal metrics along a direction of the projection vector.

19. At least one non-transitory machine-readable medium including instructions that, when executed by a machine, cause the machine to:
receive two or more signals sensed from a patient, the signals including physiological or functional signals;
generate a plurality of signal metrics from the received two or more signals;
generate a plurality of weight factors corresponding to the plurality of signal metrics, the weight factors indicating the corresponding signal metrics' reliability in representing an intensity of the pain;
generate a pain score using a combination of the plurality of signal metrics each weighted by the corresponding weight factor; and
deliver a pain therapy via an implantable neuromodulator device, the pain therapy including electrostimulation energy determined according to the pain score.

20. The at least one non-transitory machine-readable medium of claim 19, wherein the instructions, when performed by the machine, cause the machine to:
increase the electrostimulation energy in response to the pain score exceeding a threshold; or
decrease the electrostimulation energy in response to the pain score falling below a threshold.

* * * * *